(12) United States Patent
Duan et al.

(10) Patent No.: US 7,132,432 B2
(45) Date of Patent: Nov. 7, 2006

(54) HYDANTOIN DERIVATIVES AS INHIBITORS OF TUMOR NECROSIS FACTOR-ALPHA CONVERTING ENZYME (TACE)

(75) Inventors: Jingwu Duan, Yardley, PA (US); Chu-Biao Xue, Hockessin, DE (US); James Sheppeck, Newtown, PA (US); Bin Jiang, Norristown, PA (US); Lihua Chen, Boothwyn, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 359 days.

(21) Appl. No.: 10/858,978

(22) Filed: Jun. 2, 2004

(65) Prior Publication Data

US 2004/0254231 A1  Dec. 16, 2004

Related U.S. Application Data

(60) Provisional application No. 60/476,287, filed on Jun. 5, 2003.

(51) Int. Cl.
*A61K 31/147* (2006.01)
*C07D 453/02* (2006.01)

(52) U.S. Cl. .................... 514/314; 546/135
(58) Field of Classification Search ............. 514/314; 546/135
See application file for complete search history.

(56) References Cited

U.S. PATENT DOCUMENTS

| 6,800,776 | B1 | 10/2004 | Jong et al. |
| 6,930,104 | B1 * | 8/2005 | Kakihana et al. ............ 514/217 |
| 7,041,693 | B1 * | 5/2006 | Sheppeck .................... 514/385 |
| 7,049,325 | B1 * | 5/2006 | Broka et al. ................. 514/312 |
| 7,053,105 | B1 * | 5/2006 | Angibaud et al. ........... 514/313 |
| 7,064,133 | B1 * | 6/2006 | D'Angelo et al. .......... 514/311 |
| 7,074,801 | B1 * | 7/2006 | Yoshida et al. ......... 514/266.23 |

\* cited by examiner

*Primary Examiner*—Deborah C. Lambkin
(74) *Attorney, Agent, or Firm*—Jing G. Sun

(57) ABSTRACT

The present invention provides compounds of Formula (I):

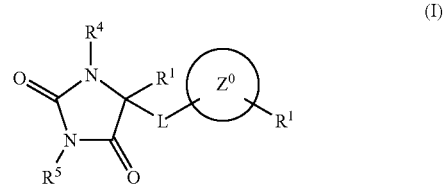

or a stereoisomer or pharmaceutically acceptable salt form thereof, wherein the variables L, $Z^0$, $R^1$, $R^4$, $R^5$, and $R^{11}$ are defined are as defined herein, which are useful as inhibitors of matrix metalloproteinases (MMP), TNF-α converting enzyme (TACE), aggrecanase, or a combination thereof.

15 Claims, No Drawings

HYDANTOIN DERIVATIVES AS INHIBITORS OF TUMOR NECROSIS FACTOR-ALPHA CONVERTING ENZYME (TACE)

CROSS-REFERENCE TO RELATED APPLICATIONS

The present application claims the priority benefit of U.S. Provisional Application No. 60/476,287, filed Jun. 5, 2003, which is expressly incorporated fully herein by reference.

FIELD OF THE INVENTION

The present invention relates generally to novel hydantoin derivatives as inhibitors of TNF-α converting enzyme (TACE), or matrix metalloproteinases (MMP) or a combination thereof, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. *Arthritis Rheum.* 1978, 21, 761–766, Woessner et al. *Arthritis Rheum.* 1983, 26, 63–68 and Woessner et al. *Arthritis Rheum.* 1984, 27, 305–312). In addition, aggrecanase has been identified as providing the specific cleavage product of proteoglycan found in RA and OA patients (Lohmander L. S. et al. *Arthritis Rheum.* 1993, 36, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al. *Lancet* 1994, 344, 1105), non-insulin dependent diabetes melitus (Lohmander, L. S. et al. *Arthritis Rheum.* 1993, 36, 1214–22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

Prostaglandins (PG) play a major role in the inflammation process and the inhibition of PG production has been a common target of anti-inflammatory drug discovery. Many NSAIDS have been found to prevent the production of PG by inhibiting the enzyme cyclooxygenase (COX). Among the two isoforms of COXs, COX-1 is constitutively expressed. COX-2 is an inducible isozyme associated with inflammation. Selective COX-2 inhibitor was believed to maintain the efficacy of traditional NSAIDs, which inhibit both isozymes, and produce fewer and less drastic side effects. As a result, development of selective COX-2 inhibitors has attracted major interest in the pharmaceutical industry. Because of the significant roles of PGs and TNF-α in inflammation, combined use of COX-2 and TACE inhibitors may have superior efficacy to either therapy alone in some inflammatory diseases.

Human macrophage elastase (MMP-12) is expressed primarily by alveolar macrophages and is responsible for tissue remodelling by proteolytically degrading elastin. MMP-12 knockout mice appear to have a diminished capacity to degrade elastin, particularly in lung tissue, and appear less susceptible to pulmonary diseases such as emphysema (Hautamaki et al. *Science* 1997, 277, 2002–2004; Lanone et al. *J. Clin. Invest.* 2002, 110, 463–474). This invention describes molecules that inhibit the activity of MMP-12 and may circumvent undesired tissue destruction found in a variety of human diseases. These novel molecules provide a means of mechanism based therapeutic intervention for diseases including but not restricted to: emphysema, asthma, chronic obstructive pulmonary disease, cystic fibrosis, cancer, metastatic disease, atherosclerosis, and aneurysm.

The compounds of the present invention act as inhibitors of MPs, in particular TACE, MMPs, and/or aggrecanase. These novel molecules are provided as anti-inflammatory compounds and cartilage protecting therapeutics. The inhibition of TACE, aggrecanase, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, the present invention provides novel hydantoin derivatives useful as TACE, MMP and/or aggrecanase inhibitors or stereoisomers or pharmaceutically acceptable salts, solvates, or prodrugs thereof.

The present invention provides pharmaceutical compositions comprising a pharmaceutically acceptable carrier and a therapeutically effective amount of at least one of the compounds of the present invention or a stereoisomer or pharmaceutically acceptable salt, solvate, or prodrug thereof.

The present invention provides a method for treating inflammatory disorders, comprising: administering to a host, in need of such treatment, a therapeutically effective amount of at least one of the compounds of the present invention or a stereoisomer or pharmaceutically acceptable salt, solvate, or prodrug thereof.

The present invention provides a method of treating a condition or disease mediated by TACE, MMPs, aggrecanase, or a combination thereof in a mammal, comprising: administering to the mammal in need of such treatment a therapeutically effective amount of a compound of the present invention or a stereoisomer or pharmaceutically acceptable salt, solvate, or prodrug thereof.

The present invention provides a method comprising: administering a compound of the present invention or a stereoisomer or pharmaceutically acceptable salt, solvate, or prodrug thereof, in an amount effective to treat a condition or disease mediated by TACE, MMPs, aggrecanase, or a combination thereof.

The present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

The present invention provides novel compounds of the present invention for use in therapy.

The present invention provides the use of novel compounds of the present invention for the manufacture of a medicament for the treatment of a condition or disease mediated by TACE, MMPs, aggrecanase, or a combination thereof.

These and other features, which will become apparent during the following detailed description, have been achieved by the inventors' discovery that compounds of Formula (I):

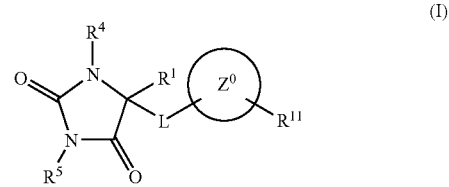

or a stereoisomer or pharmaceutically acceptable salt, solvate, or prodrug thereof, wherein L, $Z^0$, $R^1$, $R^4$, $R^5$, and $R^{11}$ are defined below, are effective as MMP, TACE and/or aggrecanase inhibitors.

DETAILED DESCRIPTION OF PREFERRED EMBODIMENTS

In a first aspect, the present invention provides, inter alia, compounds of Formula (I):

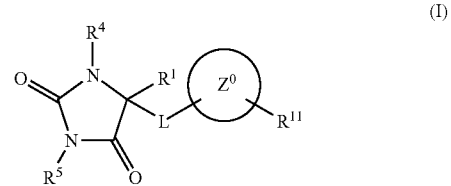

or a stereoisomer or pharmaceutically acceptable salt, solvate, or prodrug form thereof, wherein:

$R^1$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_tNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_tOC(O)(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_tNR^aC(O)(CR^aR^{a1})_s$-Q, —$(CR^aR^{a1})_tOC(O)O(CR^aR^{a1})_s$-Q, —$(CR^aR^{a1})_tOC(O)NR^a(CR^aR^{a1})_s$-Q, —$(CR^aR^{a1})_tNR^aC(O)O(CR^aR^{a1})_s$-Q, —$(CR^aR^{a1})_tNR^aC(O)NR^a(CR^aR^{a1})_s$-Q, —$(CR^aR^{a1})_rS(CR^aR^{a1})_s$-Q, —$(CR^aR^{a1})_rS(O)(CR^aR^{a1})_s$-Q, —$(CR^aR^{a1})_rS(O)_2(CR^aR^{a1})_s$-Q, —$(CR^aR^{a1})_rSO_2NR^a(CR^aR^{a1})_s$-Q, —$(CR^aR^{a1})_tNR^aSO_2(CR^aR^{a1})_s$-Q, or —$(CR^aR^{a1})_tNR^aSO_2NR^a(CR^aR^{a1})_s$-Q;

L is a bond, CO or $(CR^2R^3)_m$;

$R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_rO(CR^aR^{a1})_s$-$Q^1$, —$(CR^aR^{a1})_tNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_tNR^aC(O)(CR^aR^{a1})_s$-$Q^1$, —$(CR^aR^{a1})_rOC(O)O(CR^aR^{a1})_s$-$Q^1$, —$(CR^aR^{a1})_tOC(O)NR^a(CR^aR^{a1})_s$-$Q^1$, —$(CR^aR^{a1})_tNR^aC(O)NR^a(CR^aR^{a1})_s$-$Q^1$, —$(CR^aR^{a1}_2)_rS(O)_p(CR^aR^{a1})_s$-$Q^1$, —$(CR^aR^{a1})_rSO_2NR^a(CR^aR^{a1})_s$-$Q^1$, —$(CR^aR^{a1})_tNR^aSO_2(CR^aR^{a1})_s$-$Q^1$, or —$(CR^aR^{a1})_tNR^aSO_2NR^a(CR^aR^{a1})_s$-$Q^1$;

$R^3$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rS(O)p(CR^aR^{a1})_s$-Q, —$(CR^aR^{a1})_rSO_2NR^a(CR^aR^{a1})_s$-Q, or —$(CR^aR^{a1})_tNR^aSO_2(CR^aR^{a1})_s$-Q;

Q is, independently at each occurrence, H, CHF$_2$, CH$_2$F, CF$_3$, a C$_{3-13}$ carbocycle substituted with 0–5 R$^d$ or a 5–14 membered heterocycle consisting of carbon atoms and 1–4 heteroatoms selected from the group consisting of N, O, and S(O)$_p$, and substituted with 0–5 R$^d$;

Q$^f$ is, independently at each occurrence, H, a C$_{3-13}$ carbocycle substituted with 0–5 R$^d$ or a 5–14 membered heterocycle consisting of carbon atoms and 1–4 heteroatoms selected from the group consisting of N, NR$^7$, O, and S(O)$_p$, and substituted with 0–5 Rd;

ring Z$^0$ is a 5–7 membered heterocycle consisting of carbon atoms, 0–2 carbonyls, and 0–3 ring heteroatoms selected from O, N, NR$^7$, and S(O)$_p$;

provided that L and R$^{11}$ are not attached to the same ring atom or adjacent ring atoms of ring Z$^0$;

ring Z$^0$ is substituted with 0–2 R$^6$ and contains 0–3 ring double bonds;

R$^{11}$ is —W—U—X—Y-Z-U$^a$—X$^a$—Y$^a$—Z$^a$;

W is a bond, (CR$^a$R$^{a1}$)$_m$, C$_{2-3}$ alkenylene, or C$_{2-3}$ alkynylene;

U is absent or is O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, or NR$^{a1}$SO$_2$NR$^{a1}$;

X is absent or is C$_{1-3}$ alkylene, C$_{2-3}$ alkenylene, or C$_{2-3}$ alkynylene;

Y is absent or is O, NR$^{a1}$, S(O)$_p$, or C(O);

Z is a C$_{3-13}$ carbocycle substituted with 0–5 R$^b$ or a 5–14 membered heterocycle consisting of carbon atoms and 1–4 heteroatoms selected from the group consisting of N, O, and S(O)$_p$, and substituted with 0–5 R$^b$;

U$^a$ is absent or is O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, or NR$^{a1}$SO$_2$NR$^{a1}$;

X$^a$ is absent or is C$_{1-10}$ alkylene, C$_{2-10}$ alkenylene, or C$_{2-10}$ alkynylene;

Y$^a$ is absent or is O, NR$^{a1}$, S(O)$_p$, or C(O);

Z$^a$ is a C$_{3-13}$ carbocycle substituted with 0–5 R$^c$ or a 5–14 membered heterocycle consisting of carbon atoms and 1–4 heteroatoms selected from the group consisting of N, O, and S(O)$_p$, and substituted with 0–5 R$^c$;

provided that U, Y, Z, U$^a$, Y$^a$, and Z$^a$ do not combine to form a N—N, N—O, O—N, O—O, S(O)$_p$—O, O—S(O)$_p$ or S(O)$_p$—S(O)$_p$ group;

R$^4$ is, independently at each occurrence, H, C$_{1-6}$ alkyl, phenyl, or benzyl;

R$^a$ is, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocycle or heterocycle consisting of carbon atoms and 0–2 ring heteroatoms selected from N, NR$^{a2}$, O, and S(O)$_p$, and substituted with 0–3 R$^{c1}$;

alternatively, R$^a$ and R$^{a1}$ when attached to a nitrogen, together with the nitrogen to which they are attached, combine to form a 5 or 6 membered heterocycle consisting of carbon atoms and 0–1 additional heteroatoms selected from N, NR$^{a2}$, O, and S(O)$_p$;

R$^{a2}$ is, independently at each occurrence, C$_{1-4}$ alkyl, phenyl, or benzyl;

R$^{a3}$, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocyclic or heterocyclic ring consisting of carbon atoms and 0–2 ring heteroatoms selected from N, NR$^{a2}$, O, and S(O)$_p$, and substituted with 0–3 R$^{c1}$;

R$^b$, independently at each occurrence, C$_{1-6}$ alkyl substituted with 0–1 R$^{c1}$, —OR$^a$, —SR$^a$, Cl, F, Br, I, =O, —CN, NO$_2$, —NR$^a$R$^{a1}$, —C(O)R$^a$, —C(O)OR$^a$, —C(O)NR$^a$R$^{a1}$, —C(S)NR$^a$R$^{a1}$, NR$^a$C(O)NR$^a$R$^{a1}$, —OC(O)NR$^a$R$^{a1}$, —NR$^a$C(O)OR$^a$, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, —S(O)$_p$R$^{a3}$, CF$_3$, —CF$_2$CF$_3$, CHF$_2$, CH$_2$F, or phenyl;

R$^c$ is, independently at each occurrence, H, Cl, F, Br, I, =O, —CN, NO$_2$, CF$_3$, —CF$_2$CF$_3$, CH$_2$F, CHF$_2$, —(CR$^a$R$^{a1}$)$_r$OR$^a$, —(CR$^a$R$^{a1}$)$_r$NR$^a$R$^{a1}$, —(CR$^a$R$^{a1}$)$_r$C(=NCN)NR$^a$R$^{a1}$, —(CR$^a$R$^{a1}$)$_r$C(=NR$^a$)NR$^a$R$^{a1}$, —(CR$^a$R$^{a1}$)$_r$C(=NOR$^a$)NR$^a$R$^{a1}$, —(CR$^a$R$^{a1}$)$_r$C(O)NR$^a$OH, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$C(S)NR$^a$R$^{a1}$, —(CR$^a$R$^{a1}$)$_r$OC(O)NR$^a$R$^{a1}$, —(CR$^a$R$^{a1}$)$_r$NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —(CR$^a$R$^{a1}$)$_r$NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, (CR$^a$R$^{a1}$)$_r$—C$_{3-10}$ carbocycle substituted with 0–2 R$^{c1}$, or (CR$^a$R$^{a1}$)$_r$-5–14 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^{c1}$ is, independently at each occurrence, H, C$_{1-4}$ alkyl, —OR$^a$, Cl, F, Br, I, =O, CF$_3$, —CN, NO$_2$, —C(O)R$^a$, —C(O)OR$^a$, —C(O)NR$^a$R$^a$, or —S(O)$_p$R$^a$;

R$^d$ is, independently at each occurrence, C$_{1-6}$ alkyl, —OR$^a$, Cl, F, Br, I, =O, —CN, NO$_2$, —NR$^a$R$^{a1}$, —C(O)R$^a$, —C(O)OR$^a$, —C(O)NR$^a$R$^{a1}$, —C(S)NR$^a$R$^{a1}$, —NR$^a$C(O)NR$^a$R$^{a1}$, —OC(O)NR$^a$R$^{a1}$, —NR$^a$C(O)OR$^a$, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, —S(O)$_p$R$^{a3}$, CF$_3$, —CF$_2$CF$_3$, C$_{3-10}$ carbocycle, or a 5–14 membered heterocycle consisting of carbon atoms and 1–4 heteroatoms selected from the group consisting of N, O, and S(O)$_p$;

R$^e$ is, independently at each occurrence, H, C$_{1-6}$ alkyl, C$_{1-6}$ alkoxy, phenoxy, benzoxy, C$_{3-10}$ carbocycle substituted with 0–2 R$^{c1}$, or a 5–10 membered heterocycle consisting of carbon atoms and 1–4 heteroatoms selected from the group consisting of N, O, and S(O)$_p$, and substituted with 0–2 R$^{c1}$;

R$^4$ is H, C$_{1-4}$ alkyl, C$_{2-4}$ alkenyl, or C$_{2-4}$ alkynyl;

R$^5$ is H, C$_{1-4}$ alkyl, C$_{2-4}$ alkenyl, or C$_{2-4}$ alkynyl;

R$^6$ is, independently at each occurrence, H, Cl, F, Br, I, =O, —CN, NO$_2$, CF$_3$, —CF$_2$CF$_3$, —(CR$^a$R$^{a1}$)$_r$OR$^a$, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)R$^a$, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$C(S)NR$^a$R$^{a1}$, —(CR$^a$R$^{a1}$)$_r$OC(O)NR$^a$R$^{a1}$, (CR$^a$R$^{a1}$)$_r$NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, (CR$^a$R$^{a1}$)$_r$NR$^a$SO$_2$NR$^a$R$^{a1}$, C$_{1-6}$ alkyl substituted with 0–2 R$^{c1}$, C$_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or $(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

$R^7$ is, independently at each occurrence, H, —$(CR^aR^{a1})_t$ $NR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rC(S)NR^aR^{a1}$, —$(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or $(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

m, at each occurrence, is selected from 1, 2 and 3;
p, at each occurrence, is selected from 0, 1, and 2;
r, at each occurrence, is selected from 0, 1, 2, 3, and 4;
s, at each occurrence, is selected from 0, 1, 2, 3, and 4; and
t, at each occurrence, is selected from 1, 2, 3, and 4.

In some embodiments according to the first aspect, the present invention includes compounds of Formula (I) where $R^1$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_t NR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rOC(O)(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_tS(CR^aR^{a1})_s$-Q, —$(CR^aR^{a1})_tS(O)(CR^aR^{a1})_s$-Q, —$(CR^aR^{a1})_tS(O)_2(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q. In other embodiments, $R^1$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_tNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_tS(CR^aR^{a1})_s$-Q, —$(CR^aR^{a1})_tS(O)(CR^aR^{a1})_s$-Q, —$(CR^aR^{a1})_tS(O)_2(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q. In other embodiments, $R^1$ is Q, —$C_{1-6}$ alkylene-Q, —$C_{2-6}$ alkenylene-Q, —$C_{2-6}$ alkynylene-Q, —$(CH_2)_rO(CH_2)_s$-Q, —$(CH_2)_tNR^a(CH_2)_s$Q, —$(CH_2)_rC(O)(CH_2)_s$-Q, $(CH_2)_rC(O)O(CH_2)_s$-Q, —$(CH_2)_r C(O)NR^aR^{a1}$, —$(CH_2)_rC(O)NR^a(CH_2)_s$-Q, —$(CH_2)_tS (CH_2)_s$-Q, —$(CH_2)_tS(O)(CH_2)_s$-Q, —$(CH_2)_tS(O)_2(CH_2)_s$-Q, —$(CH_2)_rSO_2NR^a(CH_2)_s$-Q, or —$(CH_2)_rNR^aSO_2(CH_2)_s$-Q. In other embodiments, $R^1$ is Q, —$C_{1-6}$ alkylene-Q, —$C_{2-6}$ alkenylene-Q, or —$C_{2-6}$ alkynylene-Q. In other embodiments, $R^1$ is H or $C_{1-4}$ alkyl. In other embodiments, $R^1$ is H or Me.

In some embodiments according to the first aspect, the present invention includes compounds of Formula (I) where $R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_rO(CR^aR^{a1})_s$-$Q^1$, —$(CR^aR^{a1})_t NR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_rNR^aC(O)(CR^aR^{a1})_s$-$Q^1$, —$(CR^aR^{a1}R_2)_tS(O)_p(CR^aR^{a1})_s$-$Q^1$, —$(CR^aR^{a1})_rSO_2NR^a(CR^aR^{a1})_s$-$Q^1$, or —$(CR^aR^{a1})_rNR^aSO_2(CR^aR^{a1})_s$-$Q^1$. In other embodiments, $R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O (CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_rNR^aC(O)(CR^aR^{a1})_s$-$Q^1$, —$(CR^aR^{a1}_2)_tS(O)_p(CR^aR^{a1})_s$-$Q^1$, $(CR^aR^{a1})_rSO_2NR^a(CR^aR^{a1})_s$-$Q^1$, or —$(CR^aR^{a1})_rNR^aSO_2(CR^aR^{a1})_s$-$Q^1$. In other embodiments, $R^2$ is Q, —$C_{1-6}$ alkylene-$Q^1$, —$C_{2-6}$ alkenylene-$Q^1$, —$C_{2-6}$ alkynylene-$Q^1$, —$(CH_2)_rO(CH_2)_s$-$Q^1$, —$(CH_2)_tNR^a(CH_2)_s$-$Q^1$, —$(CH_2)_rC(O)(CH_2)_s$-$Q^1$, $(CH_2)_rC(O)O(CH_2)_s$-$Q^1$, —$(CH_2)_rC(O)NR^aR^{a1}$, —$(CH_2)_rC(O)NR^a(CH_2)_s$-$Q^1$, —$(CH_2)_tS(CH_2)_s$-$Q^1$, —$(CH_2)_tS(O)(CH_2)_s$-$Q^1$, $(CH_2)_t S(O)_2(CH_2)_s$-$Q^1$, —$(CH_2)_tSO_2NR^a(CH_2)_s$-$Q^1$, or —$(CH_2)_t NR^aSO_2(CH_2)_s$-$Q^1$.

In some embodiments according to the first aspect, the present invention includes compounds of Formula (I) where $R^3$ is Q, —$C_{1-6}$ alkylene-Q, —$C_{2-6}$ alkenylene-Q, —$C_{2-6}$ alkynylene-Q, —$(CH_2)_rO(CH_2)_s$-Q, —$(CH_2)_tNR^a(CH_2)_s$-Q, —$(CH_2)_rC(O)(CH_2)_s$-Q, —$(CH_2)_rC(O)O(CH_2)_s$-Q, —$(CH_2)_rC(O)NR^aR^{a1}$, —$(CH_2)_rC(O)NR^a(CH_2)_s$-Q, $(CH_2)_rNR^aC(O)(CH_2)_s$-Q, —$(CH_2)_rS(O)_p(CH_2)_s$-Q, —$(CH_2)_rSO_2NR^a(CH_2)_s$-Q, or —$(CH_2)_rNR^aSO_2(CH_2)_s$-Q. In other embodiments, $R^3$ is H, $C_{1-4}$ alkyl, $C_{2-4}$ alkenyl, $C_{2-4}$ alkynyl, phenyl, or benzyl.

In some embodiments according to the first aspect, the present invention includes compounds of Formula (I) where L is a bond, CO or $CH_2$. In other embodiments, L is a bond or $CH_2$. In other embodiments, L is a bond.

In some embodiments according to the first aspect, the present invention includes compounds of Formula (I) where W is a bond or $(CR^aR^{a1})_m$. In other embodiments, W is a bond or $CH_2$. In other embodiments, W is a bond.

In some embodiments according to the first aspect, the present invention includes compounds of Formula (I) where X is absent or is $C_{1-3}$ alkylene. In other embodiments, X is absent or is methylene.

In some embodiments according to the first aspect, the present invention includes compounds of Formula (I) where $U^a$ is absent or is O, $NR^{a1}$, C(O), $CR^a(OH)$, C(O)O, OC(O), $C(O)NR^{a1}$, $NR^{a1}C(O)$, $S(O)_p$, $S(O)_pNR^{a1}$, or $NR^{a1}S(O)_p$. In other embodiments, $U^a$ is absent or is O, $NR^{a1}$, C(O), $C(O)NR^{a1}$, $NR^{a1}C(O)$, $S(O)_p$, $S(O)_pNR^{a1}$, or $NR^{a1}S(O)_p$. In other embodiments, $U^a$ is absent or is O.

In some embodiments according to the first aspect, the present invention includes compounds of Formula (I) where $X^a$ is absent or is $C_{1-4}$ alkyl, $C_{2-4}$ alkenylene, or $C_{2-4}$ alkynylene.

In some embodiments according to the first aspect, the present invention includes compounds of Formula (I) where $Y^a$ is absent or is O or $NR^{a1}$. In other embodiments, $Y^a$ is absent or is O.

In some embodiments according to the first aspect, the present invention includes compounds of Formula (I) where $R^4$ is H, $C_{1-4}$ alkyl, $C_{2-4}$ alkenyl, or $C_{2-4}$ alkynyl. In other embodiments, $R^4$ is H or $C_1$–$C_4$ alkyl. In other embodiments, $R^4$ is H.

In some embodiments according to the first aspect, the present invention includes compounds of Formula (I) where $R^5$ is H, $C_{1-4}$ alkyl, $C_{2-4}$ alkenyl, or $C_{2-4}$ alkynyl. In other embodiments, $R^5$ is H or $C_1$–$C_4$ alkyl. In other embodiments, $R^5$ is H.

In some embodiments according to the first aspect, the present invention includes compounds of Formula (I) where $R^6$ is H, Cl, F, Br, I, =O, —CN, $NO_2$, $CF_3$, —$CF_2CF_3$, —$(CR^aR^{a1})_rOR^a$, —$(CR^aR^{a1})_rNR^aR^{a1}$, —$(CR^aR^{a1})_rC(O)R^a$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$. In other embodiments, R$^6$ is H, Cl, F, Br, I, =O, —CN, NO$_2$, CF$_3$, —CF$_2$CF$_3$, (CR$^a$R$^{a1}$)$_r$OR$^a$, —(CR$^a$R$^{a1}$)$_r$NR$^a$R$^{a1}$, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl, C$_{2-6}$ alkenyl, C$_{2-6}$ alkynyl, —(CR$^a$R$^{a1}$)$_r$C$_{3-7}$ carbocycle substituted with 0–2 R$^{c1}$, or —(CR$^a$R$^{a1}$)$_r$-5–6 membered heterocycle consisting of carbon atoms and 1–4 heteroatoms selected from the group consisting of N, O, and S(O)$_p$, and substituted with 0–2 R$^{c1}$. In other embodiments, R$^6$ is H, C$_{1-4}$ alkyl, —(CH$_2$)$_r$OH, —(CH$_2$)$_r$NH$_2$, —(CH$_2$)$_r$NHCO(C$_{1-4}$ alkyl), —(CH$_2$)$_r$NH-COO(C$_{1-4}$ alkyl), —(CH$_2$)$_r$NHSO$_2$(C$_{1-4}$ alkyl), —(CH$_2$)$_r$-phenyl substituted with 0–1 R$^{c1}$, —(CH$_2$)$_r$5–6 membered heterocycle consisting of carbon atoms and 1–4 heteroatoms selected from the group consisting of N, O, and S(O)$_p$, and substituted with 0–1 R$^{c1}$, —(CH$_2$)$_r$—NHCO-phenyl substituted with 0–1 R$^{c1}$, or —(CH$_2$)$_r$—NHCO-5–6 membered heterocycle consisting of carbon atoms and 1–4 heteroatoms selected from the group consisting of N, O, and S(O)$_p$, and substituted with 0–1 R$^{c1}$. In other embodiments, R$^6$ is H, Me, i—Pr, —CH$_2$OH, —CH$_2$NH$_2$, —CH$_2$NHCOMe, —CH$_2$NHBoc, —CH$_2$NHSO$_2$Me, 5-thiophen-2-yl, 5-morpholin-4-ylmethyl, —CH$_2$NHCO-phenyl, or —CH$_2$NHCO-4-pyridyl.

In some embodiments according to the first aspect, the present invention includes compounds of Formula (I) where R$^7$ is H, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$.

In some embodiments according to the first aspect, the present invention includes compounds of Formula (I) where Q is H, a C$_{3-6}$ cycloalkyl substituted with 0–2 R$^d$, phenyl substituted with 0–3 R$^d$ or a 5–6 membered heterocycle consisting of carbon atoms and 1–4 heteroatoms selected from the group consisting of N, O, and S(O)$_p$, and substituted with 0–3 R$^d$. In other embodiments, Q is, independently at each occurrence, H, phenyl substituted with 0–2 R$^d$, or a 5–6 membered heterocycle consisting of carbon atoms and 1–4 heteroatoms selected from the group consisting of N, O, and S(O)$_p$, and substituted with 0–2 R$^d$.

In some embodiments according to the first aspect, the present invention includes compounds of Formula (I) where Q$^1$ is H, a C$_{3-6}$ cycloalkyl substituted with 0–2 R$^d$, phenyl substituted with 0–3 R$^d$ or a 5–6 membered heterocycle consisting of carbon atoms and 1–4 heteroatoms selected from the group consisting of N, O, and S(O)$_p$, and substituted with 0–3 R$^d$. In other embodiments, Q$^1$ is, independently at each occurrence, H, phenyl substituted with 0–2 R$^d$, or a 5–6 membered heterocycle consisting of carbon atoms and 1–4 heteroatoms selected from the group consisting of N, O, and S(O)$_p$, and substituted with 0–2 R$^d$.

In some embodiments according to the first aspect, the present invention includes compounds of Formula (I) where ring Z$^0$ is a 5–6 membered heterocycle substituted with 0–2 R$^6$ and selected from: oxazolyl, isoxazolyl, dihydroisoxazolyl, thiazolyl, isothiazolyl, oxadiazolyl, thiadiazolyl, imidazolyl, imidazolinyl, imidazolidnyl, pyrrolyl, pyrrolinyl, furanyl, thienyl, pyridyl, pyrimidinyl, pyridazinyl, pyrazinyl, pyrazolyl, furyl, and triazoyl. In other embodiments, ring Z$^0$ is 4,5-dihydroisoxazol-3-yl substituted with 0–1 R$^6$, 4,5-dihydroisoxazol-5-yl substituted with 0–1 R$^6$, or isoxazol-3-yl substituted with 0–1 R$^6$.

In some embodiments according to the first aspect, the present invention includes compounds of Formula (I) Z is a C$_{3-8}$ cycloalkyl substituted with 0–5 R$^b$, a C$_{3-8}$ cycloalkenyl substituted with 0–5 R$^b$, phenyl substituted with 0–4 R$^b$, naphthyl substituted with 0–5 R$^b$, or a 5–14 membered heterocycle consisting of carbon atoms and 1–4 heteroatoms selected from the group consisting of N, O, and S(O)$_p$ and substituted with 0–5 R$^b$. In other embodiments, Z is a C$_{4-8}$ cycloalkyl substituted with 0–3 R$^b$, a C$_{4-8}$ cycloalkenyl substituted with 0–3 R$^b$, phenyl substituted with 0–4 R$^b$, naphthyl substituted with 0–5 R$^b$, or a heterocycle substituted with 0–3 R$^b$ and selected from the group: fuiranyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl. In other embodiments, Z is phenyl substituted with 0–3 R$^b$ or a heterocycle substituted with 0–2 R$^b$ and selected from the group: thienyl, Furanyl, pyridyl, pyrazinyl, pyrimidinyl, thiazolyl, oxazolyl, isoxazolyl, and imidazolyl. In other embodiments, Z$^a$ is phenyl substituted with 0–3 R$^c$, naphthyl substituted with 0–3 R$^c$, or a heterocycle substituted with 0–3 R$^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl. In other embodiments, Z$^a$ is phenyl substituted with 0–2 R$^c$.

In some embodiments according to the first aspect, the present invention includes compounds of Formula (I) where Z$^a$ is phenyl substituted with 0–3 R$^c$, naphthyl substituted with 0–3 R$^c$, or a heterocycle substituted with 0–3 R$^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl. In other embodiments, Z$^a$ is phenyl substituted with 0–3 R$^c$, naphthyl substituted with 0–3 R$^c$, or a heterocycle substituted with 0–3 R$^c$ and selected from the group:

pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl. In other embodiments, $Z^a$ is quinolinyl substituted with 0–3 $R^c$.

In a second aspect, the present invention includes compounds of Formula (I) or a stereoisomer or pharmaceutically acceptable salt, salvate or prodrug form thereof, wherein:

$R^1$ is Q, —$C_{1-6}$ alkylene-Q, —$C_{2-6}$ alkenylene-Q, —$C_{2-6}$ alkynylene-Q, —$(CR^aR^{a1})_tO(CR^aR^{a1})_s$-Q, —$(CR^aR^{a1})_tNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rOC(O)(CR^aR^{a1})_s$-Q, —$(CR^aR^{a1})_rC(O)NR^aR^{a1}$, —$(CR^aR^{a1})_rC(O)NR^a(CR^aR^{a1})_sQ$, —$(CR^aR^{a1})_rNR^aC(O)(CR^aR^{a1})_s$-Q, —$(CR^aR^{a1})_rS(CR^aR^{a1})_s$-Q, —$(CR^aR^{a1})_rS(O)(CR^aR^{a1})_s$-Q, —$(CR^aR^{a1})_rS(O)_2(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q;

$R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_rNR^aC(O)(CR^aR^{a1})_s$-$Q^1$, —$(CR^aR^{a1}{}_2)_rS(O)_p(CR^aR^{a1})_s$-$Q^1$, —$(CR^aR^{a1})_rSO_2NR^a(CR^aR^{a1})_s$-$Q^1$, or —$(CR^aR^{a1})_rNR^aSO_2(CR^aR^{a1})_s$-$Q^1$;

W is a bond or $(CR^aR^{a1})_m$;

ring $Z^0$ is a 5–6 membered heterocycle consisting of carbon atoms, 0–2 carbonyls, and 0–3 ring heteroatoms selected from O, N, $NR^7$, and $S(O)_p$;

X is absent or is $C_{1-3}$ alkylene;

$U^a$ is absent or is O, $NR^{a1}$, C(O), $CR^a(OH)$, C(O)O, OC(O), $C(O)NR^{a1}$, $NR^{a1}C(O)$, $S(O)_p$, $S(O)_pNR^{a1}$, or $NR^{a1}S(O)_p$;

$X^a$ is absent or is $C_{1-4}$ alkylene, $C_{2-4}$ alkenylene, or $C_{2-4}$ alkynylene;

$Y^a$ is absent or is O or $NR^{a1}$;

$R^a$ is, independently at each occurrence, H, $C_{1-6}$ alkyl, phenyl, or benzyl;

$R^{a1}$ is, independently at each occurrence, H, $C_{1-6}$ alkyl, $C_{2-6}$ alkenyl, $C_{2-6}$ alkynyl, or —$(CH_2)_r$-3–8 membered carbocycle or heterocycle consisting of carbon atoms and 0–2 ring heteroatoms selected from N, $NR^{a2}$, O, and $S(O)_p$;

alternatively, $R^a$ and $R^{a1}$ when attached to a nitrogen, together with the nitrogen to which they are attached, combine to form a 5 or 6 membered heterocycle consisting of carbon atoms and 0–1 additional heteroatoms selected from N, $NR^{a2}$, O, and $S(O)_p$;

$R^c$ is, independently at each occurrence, H, Cl, F, Br, =O, —CN, $NO_2$, $CF_3$, —$CF_2CF_3$, $CH_2F$, $CHF_2$, —$(CR^aR^{a1})_rOR^a$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, —$(CH_2)_r$—$C_{3-6}$ carbocycle substituted with 0–2 $R^{c1}$, or —$(CH_2)_r$-5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^d$ is, independently at each occurrence, $C_{1-6}$ alkyl, —$OR^a$, Cl, F, Br, I, =O, —CN, $NO_2$, —$NR^aR^{a1}$, —C(O)$R^a$, —C(O)$OR^a$, —C(O)$NR^aR^{a1}$, —$S(O)_2NR^aR^{a1}$, —$R^aS(O)_2R^{a3}$, —$S(O)_pR^{a3}$, $CF_3$, $C_{3-6}$ carbocycle, or a 5–6 membered heterocycle consisting of carbon atoms and 1–4 heteroatoms selected from the group consisting of N, O, and $S(O)_p$;

$R^4$ is H, $C_{1-4}$ alkyl, $C_{2-4}$ alkenyl, or $C_{2-4}$ alkynyl;

$R^5$ is H, $C_{1-4}$ alkyl, $C_{2-4}$ alkenyl, or $C_{2-4}$ alkynyl;

$R^6$ is, independently at each occurrence, H, Cl, F, Br, I, =O, —CN, $NO_2$, $CF_3$, —$CF_2CF_3$, —$(CR^aR^{a1})_rOR^a$, —$(CR^aR^{a1})_rNR^aR^{a1}$, —$(CR^aR^{a1})_rC(O)NR^aOH$, —$(CR^aR^{a1})_rC(O)R^a$, —$(CR^aR^{a1})_rC(O)(CR^aR^{a1})_sR^e$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or $(CR^aR^{a1})_r$-5–10 membered heterocycle consisting of carbon atoms and 1–4 heteroatoms selected from the group consisting of N, O, and $S(O)_p$, and substituted with 0–2 $R^{c1}$; and each $R^7$ is, independently at each occurrence, H, —$(CR^aR^{a1})_rNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—C3-10 carbocycle substituted with 0–2 $R^{c1}$, or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$.

In a third aspect, the present invention includes compounds of Formula (I) or a stereoisomer or pharmaceutically acceptable salt form thereof, wherein:

$R^1$ is Q, —$C_{1-6}$ alkylene-Q, —$C_{2-6}$ alkenylene-Q, —$C_{2-6}$ alkynylene-Q, —$(CR^aR^{a1})_tO(CR^aR^{a1})_s$-Q, —$(CR^aR^{a1})_tNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_tNR^aC(O)(CR^aR^{a1})_s$-Q, —$(CR^aR^{a1})_rS(CR^aR^{a1})_s$-Q, —$(CR^aR^{a1})_rS(O)(CR^aR^{a1})_s$-Q, —$(CR^aR^{a1})_rS(O)_2(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q;

$R^2$ is $Q^1$, —$C_{1-6}$ alkylene-$Q^1$, —$C_{2-6}$ alkenylene-$Q^1$, —$C_{2-6}$ alkynylene-$Q^1$, $(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_rNR^aC(O)(CR^aR^{a1})_s$-$Q^1$, —$(CR^aR^{a1}{}_2)_rS(O)_p(CR^aR^{a1})_s$-$Q^1$, —$(CR^aR^{a1})_rSO_2NR^a(CR^aR^{a1})_s$-$Q^1$, or —$(CR^aR^{a1})_rNR^aSO_2(CR^aR^{a1})_s$-$Q^1$;

$R^3$ is Q, —$C_{1-6}$ alkylene-Q, —$C_{2-6}$ alkenylene-Q, —$C_{2-6}$ alkynylene-Q, —$(CH_2)_rO(CH_2)_s$-Q, —$(CH_2)_rNR^a(CH_2)_s$-Q, —$(CH_2)_rC(O)(CH_2)_s$-Q, —$(CH_2)_rC(O)O(CH_2)_s$-Q, —$(CH_2)_rC(O)NR^aR^{a1}$, —$(CH_2)_rC(O)NR^a(CH_2)_s$-Q, —$(CH_2)_rNR^aC(O)(CH_2)_s$-Q, —$(CH_2)_rS(O)_p(CH_2)_s$-Q, —$(CH_2)_rSO_2NR^a(CH_2)_s$-Q, or —$(CH_2)_rNR^aSO_2(CH_2)_s$-Q;

Q is, independently at each occurrence, H, a $C_{3-10}$ carbocycle substituted with 0–3 $R^d$ or a 5–10 membered heterocycle consisting of carbon atoms and 1–4 heteroatoms selected from the group consisting of N, O, and $S(O)_p$, and substituted with 0–3 $R^d$;

$Q^1$ is, independently at each occurrence, H, a $C_{3-10}$ carbocycle substituted with 0–3 $R^d$ or a 5–10 membered heterocycle consisting of carbon atoms and 1–4 heteroatoms selected from the group consisting of N, O, and $S(O)_p$, and substituted with 0–3 $R^d$;

ring $Z^0$ is a 5–6 membered heterocycle substituted with 0–2 $R^6$ and selected from: oxazolyl, isoxazolyl, dihydroisoxazolyl, thiazolyl, isothiazolyl, oxadiazolyl, thiadiazolyl, imidazolyl, imidazolinyl, imidazolidnyl, pyrrolyl, pyrrolinyl, furanyl, thienyl, pyridyl, pyrimidinyl, pyridazinyl, pyrazinyl, pyrazolyl, furyl, and triazoyl;

$U^a$ is absent or is O, $NR^{a1}$, C(O), C(O)$NR^{a1}$, $NR^{a1}$C(O), $S(O)_p$, $S(O)_p NR^{a1}$, or $NR^{a1}S(O)_p$;

X is absent or is methylene or ethylene;

Z is a $C_{3-8}$ cycloalkyl substituted with 0–5 $R^b$, a $C_{3-8}$ cycloalkenyl substituted with 0–5 $R^b$, phenyl substituted with 0–4 $R^b$, naphthyl substituted with 0–5 $R^b$, or a 5–14 membered heterocycle consisting of carbon atoms and 1–4 heteroatoms selected from the group consisting of N, O, and $S(O)_p$ and substituted with 0–5 $R^b$;

$U^a$ is absent or is O, $NR^{a1}$, C(O), C(O)$NR^{a1}$, $NR^{a1}$C(O), $S(O)_p$, $S(O)_p NR^{a1}$, or $NR^{a1}S(O)_p$;

$R^{a3}$, independently at each occurrence, H, $C_{1-6}$ alkyl, $C_{2-6}$ alkenyl, or —(CH$_2$)$_r$-3–8 membered carbocyclic or heterocyclic ring consisting of carbon atoms and 0–2 ring heteroatoms selected from N, $NR^{a2}$, O, and $S(O)_p$ and substituted with 0–3 $R^{c1}$;

$R^c$ is, independently at each occurrence, H, Cl, F, Br, =O, $CF_3$, —$CF_2CF_3$, $CH_2F$, $CHF_2$, —$(CR^aR^{a1})_rOR^a$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, —(CH$_2$)$_r$—$C_{3-6}$ cycloalkyl substituted with 0–1 $R^{c1}$, phenyl substituted with 0–2 $R^{c1}$, or —(CH$_2$)$_r$-5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^d$ is, independently at each occurrence, $C_{1-6}$ alkyl, —$OR^a$, Cl, F, Br, I, =O, —$NR^aR^{a1}$, —C(O)$R^a$, —C(O)$OR^a$, —C(O)$NR^aR^{a1}$, —$S(O)_2NR^aR^{a1}$, —$NR^aS(O)_2R^{a3}$, —$S(O)_pR^{a3}$, $CF_3$, or phenyl;

$R^4$ is H;

$R^5$ is H;

$R^6$ is, independently at each occurrence, H, Cl, F, Br, I, =O, —CN, $NO_2$, $CF_3$, —$CF_2CF_3$, —$(CR^aR^{a1})_rOR^a$, —$(CR^aR^{a1})_rNR^aR^{a1}$, —$(CR^aR^{a1})_rC(O)R^a$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or $(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

r, at each occurrence, is selected from 0, 1, 2, and 3;

s, at each occurrence, is selected from 0, 1, 2, and 3; and t, at each occurrence, is selected from 1, 2, and 3.

In a fourth aspect, the present invention includes compounds of Formula (I) or a stereoisomer or pharmaceutically acceptable salt form thereof, wherein:

$R^1$ is Q, —$C_{1-6}$ alkylene-Q, —$C_{2-6}$ alkenylene-Q, —$C_{2-6}$ alkynylene-Q, —(CH$_2$)$_r$O(CH$_2$)$_s$-Q, —(CH$_2$)$_r$NR$^a$(CH$_2$)$_s$-Q, —(CH$_2$)$_r$C(O)(CH$_2$)$_s$-Q, —(CH$_2$)$_r$C(O)O(CH$_2$)$_s$-Q, —(CH$_2$)$_r$C(O)NR$^a$R$^{a1}$, —(CH$_2$)$_r$C(O)NR$^a$(CH$_2$)$_s$-Q, —(CH$_2$)$_r$S(CH$_2$)$_s$-Q, —(CH$_2$)$_r$S(O)(CH$_2$)$_s$-Q, —(CH$_2$)$_r$S(O)$_2$(CH$_2$)$_s$-Q, —(CH$_2$)$_r$SO$_2$NR$^a$(CH$_2$)$_s$-Q, or —(CH$_2$)$_t$NR$^a$SO$_2$(CH$_2$)$_s$-Q;

$R^2$ is Q, —$C_{1-6}$ alkylene-$Q^1$, —$C_{2-6}$ alkenylene-$Q^1$, —$C_{2-6}$ alkynylene-$Q^1$, —(CH$_2$)$_r$O(CH$_2$)$_s$-$Q^1$, —(CH$_2$)$_r$NR$^a$(CH$_2$)$_s$-$Q^1$, —(CH$_2$)$_r$C(O)(CH$_2$)$_s$-$Q^1$, —(CH$_2$)$_r$C(O)O(CH$_2$)$_s$-$Q^1$, —(CH$_2$)$_r$C(O)NR$^a$R$^{a1}$, —(CH$_2$)$_r$C(O)NR$^a$(CH$_2$)$_s$-$Q^1$, —(CH$_2$)$_r$S(CH$_2$)$_s$-$Q^1$, —(CH$_2$)$_r$S(O)(CH$_2$)$_s$-$Q^1$, —(CH$_2$)$_r$S(O)$_2$(CH$_2$)$_s$-$Q^1$, —(CH$_2$)$_r$SO$_2$NR$^a$(CH$_2$)$_s$-$Q^1$, or —(CH$_2$)$_t$NR$^a$SO$_2$(CH$_2$)$_s$-$Q^1$;

$R^3$ is H, $C_{1-4}$ alkyl, $C_{2-4}$ alkenyl, $C_{2-4}$ alkynyl, phenyl, or benzyl;

Q is, independently at each occurrence, H, a $C_{3-6}$ cycloalkyl substituted with 0–2 $R^d$, phenyl substituted with 0–3 $R^d$ or a 5–6 membered heterocycle consisting of carbon atoms and 1–4 heteroatoms selected from the group consisting of N, O, and $S(O)_p$, and substituted with 0–3 $R^d$;

$Q^1$ is, independently at each occurrence, H, a $C_{3-6}$ cycloalkyl substituted with 0–2 $R^d$, phenyl substituted with 0–3 $R^d$ or a 5–6 membered heterocycle consisting of carbon atoms and 1–4 heteroatoms selected from the group consisting of N, O, and $S(O)_p$, and substituted with 0–3 $R^d$;

Z is a $C_{4-8}$ cycloalkyl substituted with 0–3 $R^b$, a $C_{4-8}$ cycloalkenyl substituted with 0–3 $R^b$, phenyl substituted with 0–4 $R^b$, naphthyl substituted with 0–5 $R^b$, or a heterocycle substituted with 0–3 $R^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl;

$Z^a$ is phenyl substituted with 0–3 $R^c$, naphthyl substituted with 0–3 $R^c$, or a heterocycle substituted with 0–3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

$R^a$ is, independently at each occurrence, H, $C_{1-6}$ alkyl, phenyl, or benzyl;

$R^{a1}$ is, independently at each occurrence, H, $C_{1-6}$ alkyl, phenyl, or benzyl;

$R^{a3}$ is, independently at each occurrence, H, $C_{1-6}$ alkyl, phenyl, or benzyl;

$R^c$ is, independently at each occurrence, H, Cl, F, Br, =O, $CF_3$, $-CF_2CF_3$, $CH_2F$, $CHF_2$, $-(CR^aR^{a1})_rOR^a$, $(CR^aR^{a1})_r NR^aR^{a1}$, $(CR^aR^{a1})_rC(O)R^{a1}$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or a 5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds; and $R^6$ is, independently at each occurrence, H, Cl, F, Br, I, =O, —CN, $NO_2$, $CF_3$, $-CF_2CF_3$, $-(CR^aR^{a1})_rOR^a$, $-(CR^aR^{a1})_rNR^aR^{a1}$, $-(CR^aR^{a1})_rC(O)(CR^aR^{a1})_sR^e$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, $C_{1-6}$ alkyl, $C_{2-6}$ alkenyl, $C_{2-6}$ alkynyl, $(CR^aR^{a1})_rC_{3-7}$ carbocycle substituted with 0–2 $R^{c1}$, or $(CR^aR^{a1})_r$-5–6 membered heterocycle consisting of carbon atoms and 1–4 heteroatoms selected from the group consisting of N, O, and $S(O)_p$, and substituted with 0–2 $R^{c1}$.

In a fifth aspect, the present invention includes compounds of Formula (I) or a stereoisomer or pharmaceutically acceptable salt form thereof, wherein:

$R^1$ is Q, $-C_{1-6}$ alkylene-Q, $-C_{2-6}$ alkenylene-Q, or $-C_{2-6}$ alkynylene-Q;

each Q is, independently at each occurrence, H, phenyl substituted with 0–2 $R^d$, or a 5–6 membered heterocycle consisting of carbon atoms and 1–4 heteroatoms selected from the group consisting of N, O, and $S(O)_p$, and substituted with 0–2 $R^d$;

L is a bond, CO or $CH_2$;

X is absent or is methylene;

Y is absent or is O;

Z is phenyl substituted with 0–3 $R^b$ or a heterocycle substituted with 0–2 $R^b$ and selected from the group: thienyl, Furanyl, pyridyl, pyrazinyl, pyrimidinyl, thiazolyl, oxazolyl, isoxazolyl, and imidazolyl;

$U^a$ is absent or is O;

$X^a$ is absent or is $C_{1-4}$ alkylene, $C_{2-4}$ alkenylene, or $C_{2-4}$ alkynylene;

$Y^a$ is absent or is O;

$R^a$ is, independently at each occurrence, H or $C_{1-4}$ alkyl;

$R^{a1}$ is, independently at each occurrence, H or $C_{1-4}$ alkyl;

$R^{a3}$, independently at each occurrence, H, $C_{1-4}$ alkyl, phenyl, or benzyl;

$R^c$ is, independently at each occurrence, H, $C_{1-6}$ alkyl, $C_{2-6}$ alkenyl, $C_{2-6}$ alkynyl, Cl, F, Br, =O, $CF_3$, $CH_2F$, $CHF_2$, $-(CR^aR^{a1})_rOR^a$, $(CR^aR^{a1})_rNR^aR^{a1}$, $-(CR^aR^{a1})_rC(O)R^{a1}$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, or phenyl;

alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^e$ is, independently at each occurrence, H, $C_{1-6}$ alkyl, $C_{1-6}$ alkoxy, phenoxy, benzoxy, $C_{3-6}$ carbocycle substituted with 0–2 $R^{c1}$, and a 5–6 membered heterocycle consisting of carbon atoms and 1–4 heteroatoms selected from the group consisting of N, O, and $S(O)_p$, and substituted with 0–2 $R^{c1}$; and $R^6$ is, independently at each occurrence, H, Cl, F, Br, I, =O, —CN, $NO_2$, $CF_3$, $-CF_2CF_3$, $-(CH_2)_rOR^a$, $-(CH_2)_rNR^aR^{a1}$, $-(CH_2)_rC(O)R^a$, $-(CH_2)_rC(O)(CH_2)_sR^e$, $-(CH_2)_rC(O)OR^{a1}$, $-(CH_2)_rC(O)NR^aR^{a1}$, $-(CH_2)_rS(O)_pR^{a3}$, $-(CH_2)_rSO_2NR^aR^{a1}$, $C_{1-4}$ alkyl substituted with 0–1 $R^{c1}$, $C_{2-4}$ alkenyl substituted with 0–1 $R^{c1}$, $C_{2-4}$ alkynyl substituted with 0–1 $R^{c1}$, $-(CH_2)_r-C_{3-6}$ carbocycle substituted with 0–2 $R^{c1}$, or $-(CH_2)_r$-5–6 membered heterocycle consisting of carbon atoms and 1–4 heteroatoms selected from the group consisting of N, O, and $S(O)_p$, and substituted with 0–2 $R^{c1}$.

In a sixth aspect, the present invention includes compounds of Formula (I) or a stereoisomer or pharmaceutically acceptable salt form thereof, wherein:

Z is phenyl substituted with 0–1 $R^b$;

$Z^a$ is phenyl substituted with 0–3 $R^c$, naphthyl substituted with 0–3 $R^c$, or a heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

$R^b$ is, independently at each occurrence, $C_{1-6}$ alkyl, —$OR^a$, Cl, F, Br, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, or $CF_3$;

$R^c$ is, independently at each occurrence, H, $C_{1-6}$ alkyl, $C_{2-6}$ alkenyl, $C_{2-6}$ alkynyl, Cl, F, Br, =O, $CF_3$, —$(CH_2)_rOR^a$, —$(CH_2)_rNR^aR^{a1}$, —$(CH_2)_rC(O)R^{a1}$, —$(CH_2)_rC(O)OR^{a1}$, —$(CH_2)_rC(O)NR^aR^{a1}$, —$(CH_2)_rNR^aC(O)R^{a1}$, $(CH_2)_rS(O)_pR^{a3}$, —$(CH_2)_rSO_2NR^aR^{a1}$, or —$(CH_2)_rNR^aSO_2R^{a3}$;

alternatively, when two $R^c$ groups are attached to adjacent carbon atoms, together with the carbon atoms to which they are attached they form a 5–6 membered carbocyclic or heterocyclic ring consisting of: carbon atoms and 0–1 heteroatoms selected from the group consisting of N, O, and $S(O)_p$; and $R^e$ is, independently at each occurrence, H, $C_{1-6}$ alkyl, $C_{1-6}$ alkoxy, phenoxy, benzoxy, phenyl substituted with 0–1 $R^{c1}$, or a 5–6 membered heterocycle consisting of carbon atoms and 1–4 heteroatoms selected from the group consisting of N, O, and $S(O)_p$, and substituted with 0–1 $R^{c1}$.

In a seventh aspect, the present invention includes compounds of Formula (Ia):

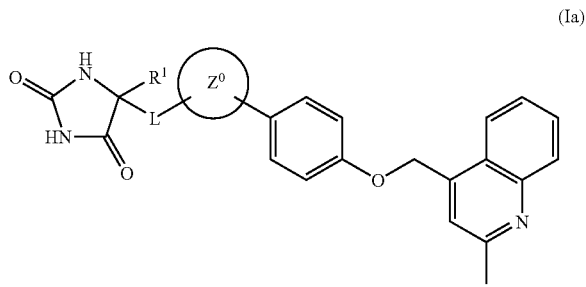

(Ia)

or a stereoisomer or pharmaceutically acceptable salt form thereof, wherein:

$R^1$ is H or $C_{1-4}$ alkyl;

L is a bond or —$CH_2$—;

ring $Z^0$ is 4,5-dihydroisoxazol-3-yl substituted with 0–1 $R^6$, 4,5-dihydroisoxazol-5-yl substituted with 0–1 $R^6$, isoxazol-3-yl substituted with 0–1 $R^6$, or isoxazol-5-yl substituted with 0–1 $R^6$;

$R^6$ is H, $C_{1-4}$ alkyl, —$(CH_2)_r$OH, —$(CH_2)_r$NH$_2$, —$(CH_2)_r$NHCO($C_{1-4}$ alkyl), —$(CH_2)_r$NHCOO($C_{1-4}$ alkyl), —$(CH_2)_r$NHSO$_2$($C_{1-4}$ alkyl), —$(CH_2)_r$-phenyl substituted with 0–1 $R^{c1}$, —$(CH_2)_r$-5–6 membered heterocycle consisting of carbon atoms and 1–4 heteroatoms selected from the group consisting of N, O, and S(O)$_p$, and substituted with 0–1 $R^{c1}$, —$(CH_2)_r$—NHCO-phenyl substituted with 0–1 $R^{c1}$, or —$(CH_2)_r$—NHCO-5–6 membered heterocycle consisting of carbon atoms and 1–4 heteroatoms selected from the group consisting of N, O, and S(O)$_p$, and substituted with 0–1 $R^{c1}$; and r, at each occurrence, is 0 or 1.

In a eighth aspect, the present invention includes compounds of Formula (Ia) or a stereoisomer or pharmaceutically acceptable salt form thereof, wherein:

$R^1$ is H or Me;

L is a bond or —$CH_2$—; and $R^6$ is H, Me, i-Pr, —$CH_2$OH, —$CH_2$NH$_2$, —$CH_2$NHCOMe, —$CH_2$NHBoc, —$CH_2$NHSO$_2$Me, 5-thiophen-2-yl, 5-morpholin-4-ylmethyl, —$CH_2$NHCO-phenyl, or —$CH_2$NHCO-4-pyridyl.

In a ninth aspect, the present invention provides a compound selected from Examples 1–15 or a stereoisomer or pharmaceutically acceptable salt form thereof.

In another embodiment, the present invention provides a novel process for making a compound of the present invention or a stereoisomer or pharmaceutically acceptable salt or solvate thereof.

In another embodiment, the present invention provides a novel intermediate for making a compound of the present invention or a stereoisomer or pharmaceutically acceptable salt or solvate thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating or preventing an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt form thereof.

In another embodiment, the present invention provides a novel method comprising: administering a compound of the present invention or a pharmaceutically acceptable salt form thereof in an amount effective to treat a condition or disease mediated by MMPs, TACE, aggrecanase, or a combination thereof.

In another embodiment, the present invention provides a novel method of treating a disease or condition selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, aggrecanase, or a combination thereof.

In another embodiment, the present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of an inflammatory disorder.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat an inflammatory disorder.

In another preferred embodiment, the present invention provides a novel article of manufacture, further comprising:

(d) a second container; wherein components (a) and (b) are located within the second container and component (c) is located within or outside of the second container.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

Definitions

Compounds of this invention may have one or more asymmetric centers. Unless otherwise indicated, all chiral (enantiomeric and diastereomeric) and racemic forms of compounds of the present invention are included in the present invention. Many geometric isomers of olefins, C═N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$–$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_2$–$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_2$–$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2C_5$, and the like.

The term "alkoxy" or "alkyloxy" refers to an O-alkyl group. "$C_1$–$C_6$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_1$–$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4H-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-Oxadiazolyl, 1,2,4-Oxadiazolyl, 1,2,5-Oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, imidazo[1,2-a]pyridinyl, imidazo[1,5-a]pyridinyl, and pyrazolo[1,5-a]pyridinyl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0–3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

The term "independently selected from", "independently at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with MCPBA and or hydrogen peroxides to afford other compounds of this invention. Thus, all shown amines are considered to cover both the shown amine and its N-oxide (N→O) derivative.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Prodrugs" refer to inactive compounds that can be converted upon absorption by a mammalian subject to an active compound of the present invention. Prodrugs of the compounds of the present invention can be prepared by modifing functional groups present in the compounds of the present invention in such a way that the modifications are cleaved in vivo to produce the parent compounds. Examples of prodrugs include, but are not limited to, acetate, formate and benzoate derivatives of alcohol and amine functional groups in the compounds of the present invention. Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa. "Therapeutically effective amount" is also intended to include an amount of the combination of compounds claimed that is effective to inhibit factor XIa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, which is incorporated herein by reference in its entirety.

Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

All references cited herein are hereby incorporated in their entirety herein by reference.

Hydantoin heterocycles of Formula (I) in the present invention can be synthesized using a variety of literature methods both in solution and on solid support (see for instance, Matthews, J. and Rivero, R. A. *J. Org Chem.* 1997, 62, 6090–6092). Several syntheses of these heterocycles are listed in Scheme 1.

Scheme 1. Hydantoin Synthetic Routes
(1) hydantoins from α-amino acids and esters

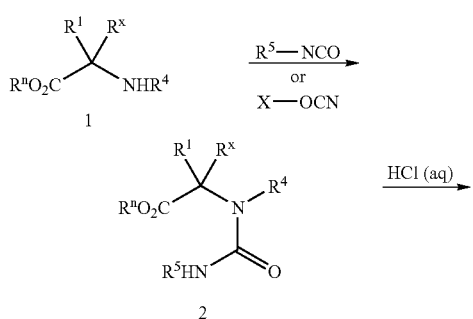

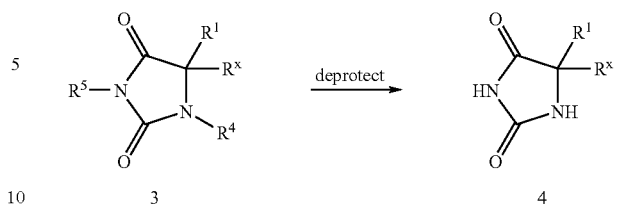

(2) hydantoins from ketones and aldehydes (the Bucherer-Bergs reaction)

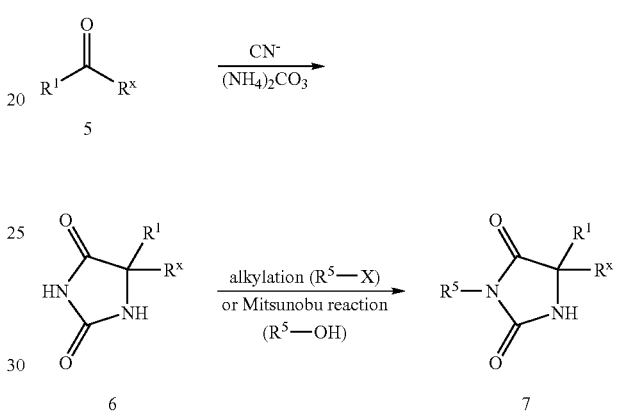

(3) hydantoins from amino nitriles (the Strecker Reaction)

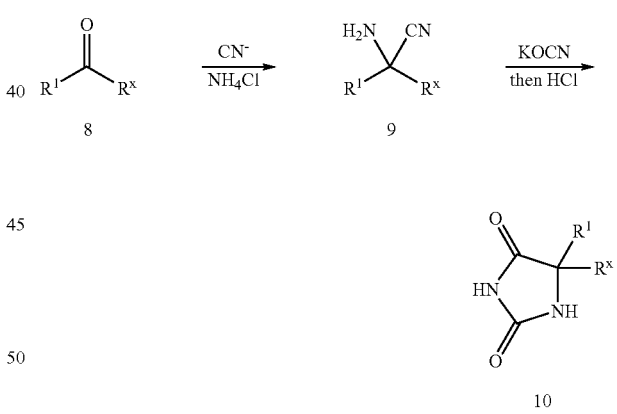

(4) hydantoins from carboxylic acids

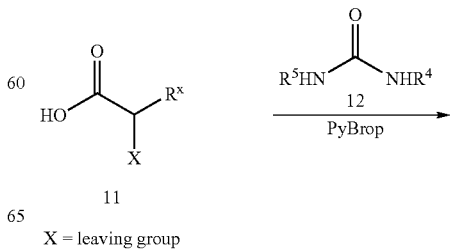

X = leaving group

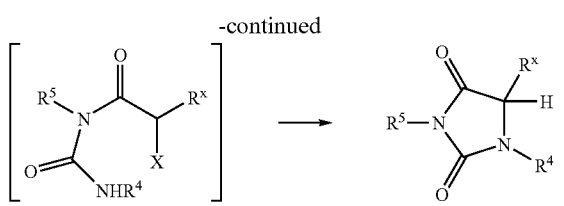

(5) hydantoins from α-amino amides

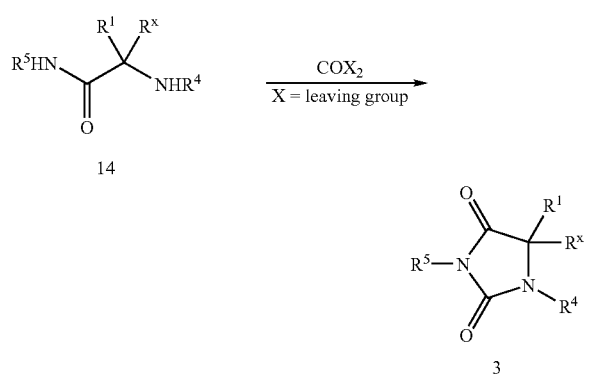

(6) hydantoins from α-amino esters

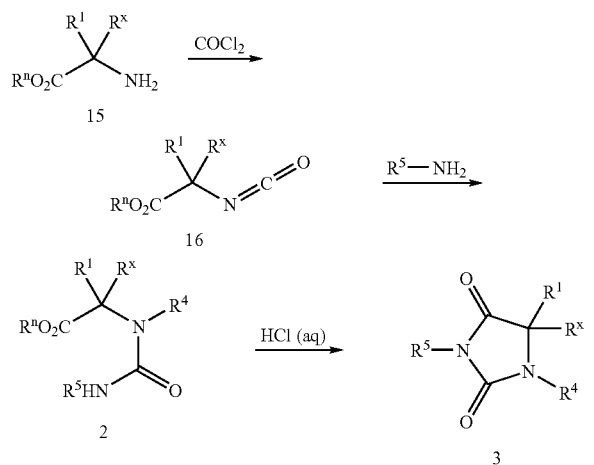

Route (1) in Scheme 1 involves reacting an α-amino acid (or its ester) 1 possessing variable substitution with either an isocyanate to form an intermediate substituted urea or with a cyanic acid salt (X—OCN; wherein X is a cationic group eg. $Na^+$, $Me_4N^+$, etc.) to form an intermediate unsubstituted urea 2. Treatment with acid results in cyclization to form the fully functionalized hydantoin core structure 3 that can be optionally deprotected if $R^4$ and $R^5$ are protecting groups (e.g. benzyl, trimethylsilyl, etc.; see Greene and Wuts, "Protecting Groups in Organic Synthesis" 3rd Ed. 1999) to give compound 4.

Route (2) in Scheme 1 is the classical Bucherer-Bergs reaction used to form hydantoins from ketones or aldehydes 5 in the presence of cyanide ion and ammonium carbonate (see Bucherer and Steiner J. Prakt. Chem. 1934, 140, 291).

The resulting hydantoin 6 can be optionally functionalized at the 3-position using standard alkylation or a Mitsunobu reaction known to one skilled in the art to give 7.

Route (3) in Scheme 1 is another route to hydantoins that takes advantage of the Strecker reaction (see Sacripante, G. and Edward, J. T. Can J. Chem. 1982, 60, 1982–1988). Treatment of ketone 8 with cyanide ion and ammonium chloride gives an intermediate amino nitrile 9 that can further react with potassium cyanate followed by acid catalyzed cyclization to give the product of substructure 10. Alternatively, intermediate 9 can be hydrolyzed in aqueous acid to form α-amino acids that can serve as starting materials for Route (1). In this respect, a variety of hydantoins can be synthesized following literature procedures used to make α-amino acids.

Route (4) in Scheme 1 shows a method for making hydantoins by coupling substituted ureas to a carboxylic acid that contains a leaving group at the α position 11 (e.g. α-chloro carboxylate). Coupling the acid 11 and a urea 12 can be accomplished using a peptide coupling reagent (e.g. PyBrop) or by converting the carboxyic acid to an acid chloride and reacting it with the urea. The urea intermediate then undergoes an intramolecular SN2 reaction to yield the final product 13.

Route (5) in Scheme 1 illustrates hydantoin synthesis from α-amino amides 14, which are made using well-established amide bond forming reactions known to one skilled in the art. Treatment of 14 with phosgene (and equivalents such as carbonyl diimidazole) directly yields the final substituted hydantoin 3.

Route (6) in Scheme 1 depicts a method used by Nowick et al. (J. Org. Chem. 1996, 61, 3929–3934) to synthesize hydantoins from amino acid esters. Treatment of an amino acid ester 15 with phosgene provides an intermediate isocyanate of structure 16. This intermediate is then reacted with variously susbstituted amines to give a urea of structure 2 which is cyclized under acidic conditions as described earlier to give the product heterocycle 3.

A series of hydantoins where $Z^0$ is an isoxazole can be prepared following a sequence outlined in Scheme 2. Alcohol 18 is protected as TBS ether (19). Ozonolysis followed by reduction with $PPh_3$ provides oxime 21 after reaction with hydroxylamine. Treatment of 21 with NBS provides nitrile oxide, which is reacted in situ with alkyne 22 to provide isoxazole 23. The silyl ether of 23 is hydrolyzed using TBAF, and the free alcohol oxidized to ketone 25 using the Dess-Martin periodinane. Bucherer-Bergs reaction converts ketone 25 to hydantoin 26.

Scheme 2

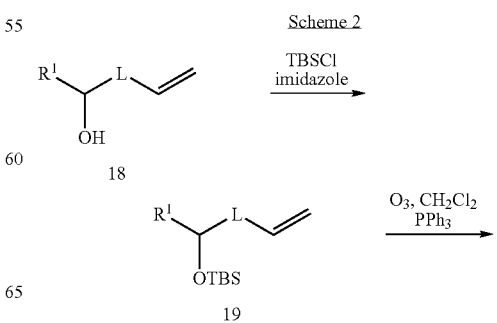

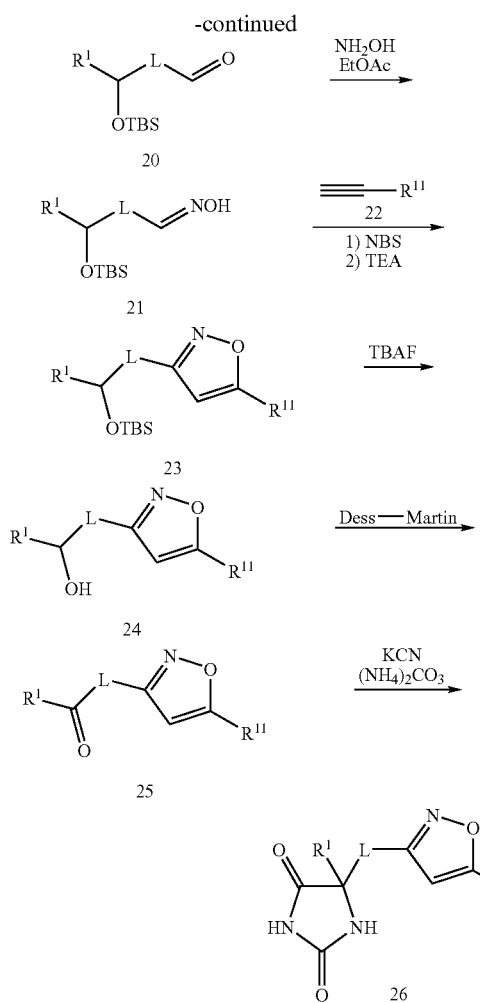

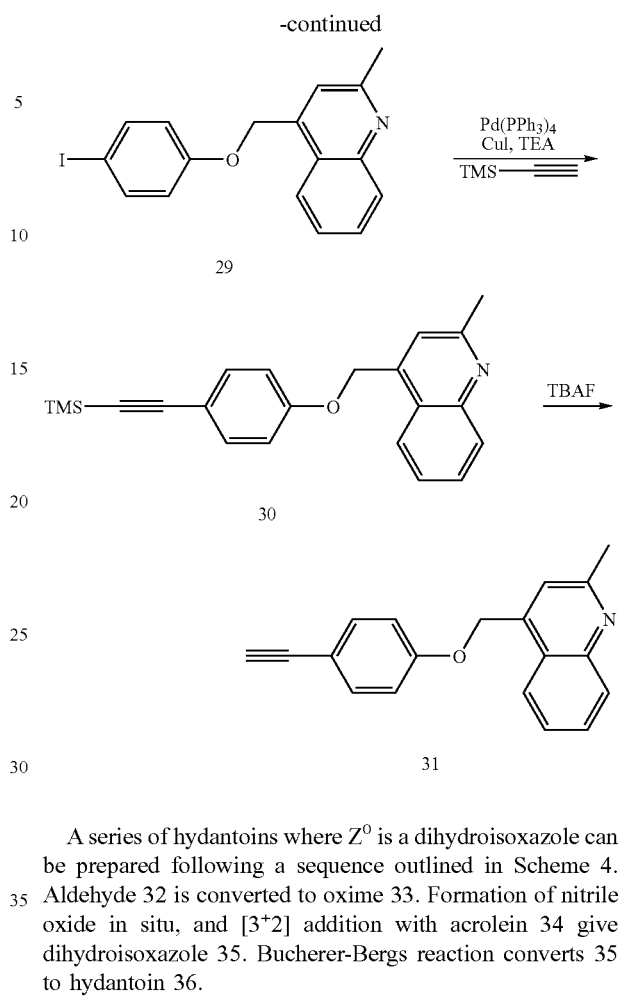

Alkyne 22 used in the aforementioned route can be synthesized in several approaches. A representative synthesis is illustrated in Scheme 3. Alkylation of 4-iodophenol (27) with 4-Chloromethyl-2-methylquinoline (28) is effected with $K_2CO_3$. Sonogashira coupling (*Tetrahedron Lett.* 1975, 16, 4467) of the resulting iodide (29) with trimethylsilylacetylene followed by desilylation provides alkyne 31, which is used for isoxazole formation as depicted in Scheme 2.

Scheme 3

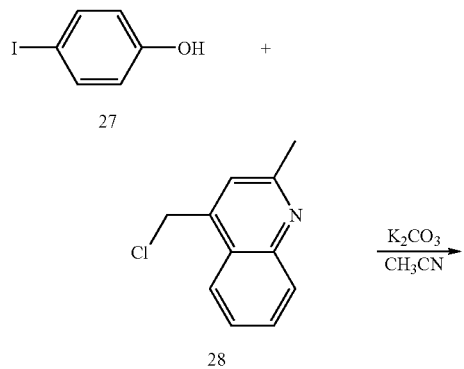

A series of hydantoins where $Z^0$ is a dihydroisoxazole can be prepared following a sequence outlined in Scheme 4. Aldehyde 32 is converted to oxime 33. Formation of nitrile oxide in situ, and [3+2] addition with acrolein 34 give dihydroisoxazole 35. Bucherer-Bergs reaction converts 35 to hydantoin 36.

Scheme 4

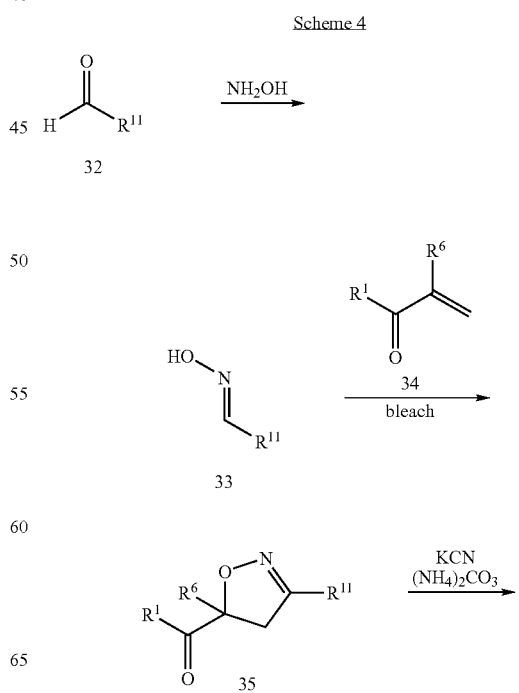

-continued

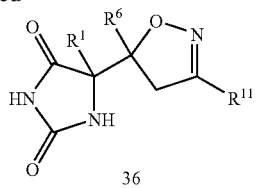
36

A series of hydantoins where $Z^0$ is another regiosomer of dihydroisoxazoles can be prepared following a sequence outlined in Scheme 5. Oxime 21, prepared using the sequence outlined in Scheme 2, is reacted with olefin 37 to give isoxazole 38 using conditions described before. The silyl ether of 38 is hydrolyzed using TBAF, and the free alcohol is oxidized to ketone 40 using the Dess-Martin periodinane. Bucherer-Bergs reaction converts 40 to hydantoin 41.

Scheme 5

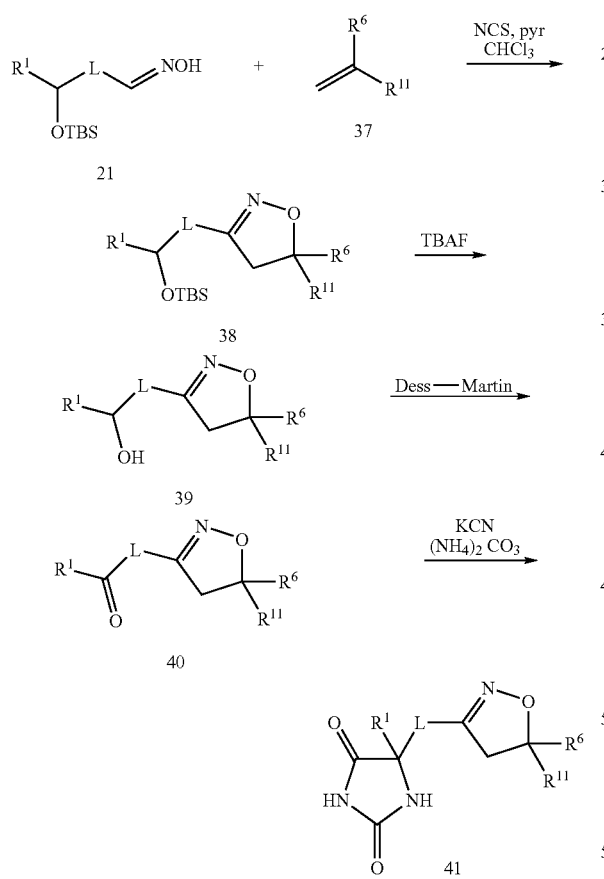

cuprate to the acetylene moiety of 45 gives olefin 46. Coupling of 46 and iodobenzene 47 using $Pd(OAc)_2$/DPPE catalysts provides olefin 37d. In Route D, acetophenone 42 is brominated with phenyltrimethylammonium tribromide. The resulting bromide 48 is converted to 49 via nucleophilic displacement with morpholine. Olefin 37e is prepared from 49 using Wittig olefination. Olefins 37a–e are used as starting material for the [3+2] cycloaddition shown in Scheme 5.

Scheme 6

Route A:

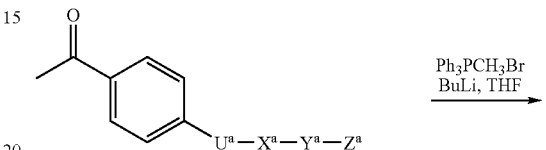
42

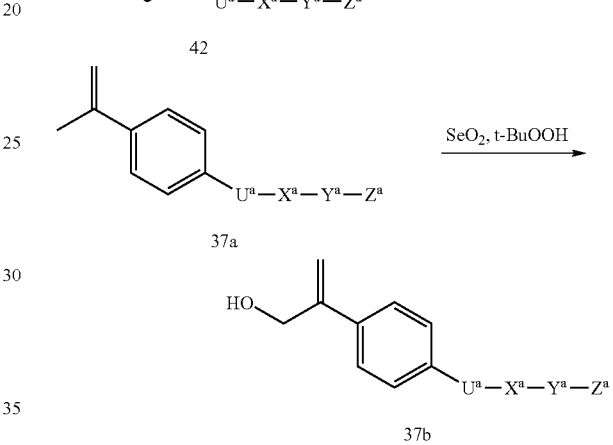

Route B:

42

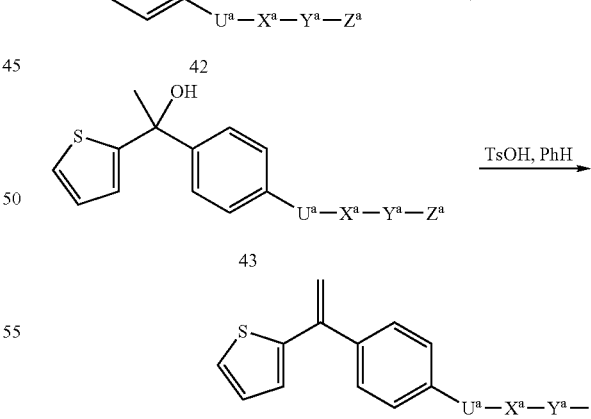

The 1,1-disubstituted olefin 37 can be synthesized in a variety of fashion. Several routes leading to derivatives where $R^{11}$ is a substituted phenyl group are outlined in Scheme 6. In Route A, acetophenone 42 is reacted with a methyl ylide to give olefin 37a. Allylic oxidation with $SeO_2$ provides alcohol 37b. In Route B, nucleophilic addition of lithiated thiophen to acetophenone 42 gives tertiary alcohol, which is dehydrated upon treatment with TsOH to provide olefin 37c. In Route C, propargyl amine (44) is protected with di-t-butyl dicarbonate. Addition of trimethylsilyl Route C:

44

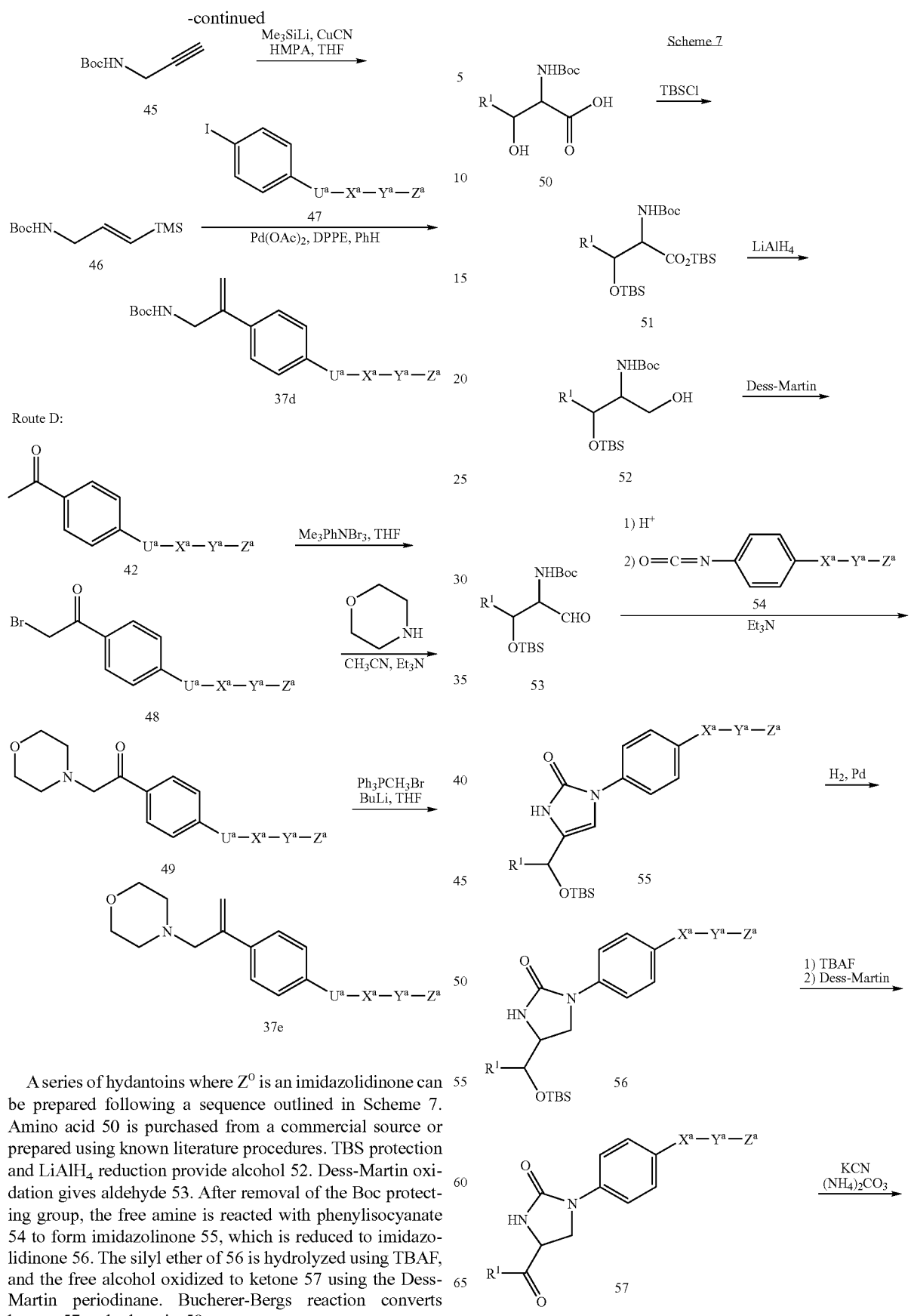

A series of hydantoins where $Z^o$ is an imidazolidinone can be prepared following a sequence outlined in Scheme 7. Amino acid 50 is purchased from a commercial source or prepared using known literature procedures. TBS protection and LiAlH$_4$ reduction provide alcohol 52. Dess-Martin oxidation gives aldehyde 53. After removal of the Boc protecting group, the free amine is reacted with phenylisocyanate 54 to form imidazolinone 55, which is reduced to imidazolidinone 56. The silyl ether of 56 is hydrolyzed using TBAF, and the free alcohol oxidized to ketone 57 using the Dess-Martin periodinane. Bucherer-Bergs reaction converts ketone 57 to hydantoin 58.

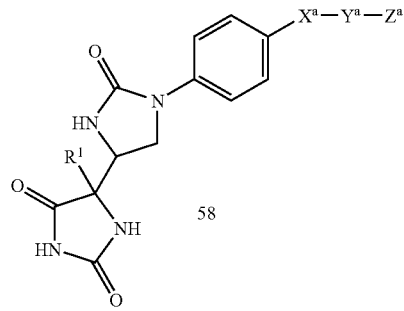

A series of hydantoins where $Z^o$ is pyrrolinone can be prepared following a sequence outlined in Scheme 8. Phenol 59 is prepared in 4 steps from p-acetophenol according to known literature procedures (*Chem. Pharm. Bull.* 1971, 19, 227–246). Following protection of the phenol group with TBSCl, the p-methoxybenzylamine moiety is protected with Cbz and the PMB group removed by CAN oxidation to give ketone 61. Aldehyde 64 can be prepared from α-methyl serine 62 ($R^1$=Me) or serine derivatives ($R^1$=other than Me, *Helv. Chim. Acta* 1987, 70, 1194–1216). Aldol condensation of 61 and 64 gives 65 which is oxidized to β-diketo compound 66. Removal of the Cbz group induces the ring closure to form the pyrrolinone 67 (*Bioorg. Med. Chem.* 1996, 4, 1021–1034). The TBS ether is then cleaved and the free phenol reacted with $ClCH_2Z^a$ (68) to give compound 69. Finally, removal of the Boc group, coupling of the free nitrogen with potassium isocyanate and basic treatment of the resulting urea give the hydantoin 70.

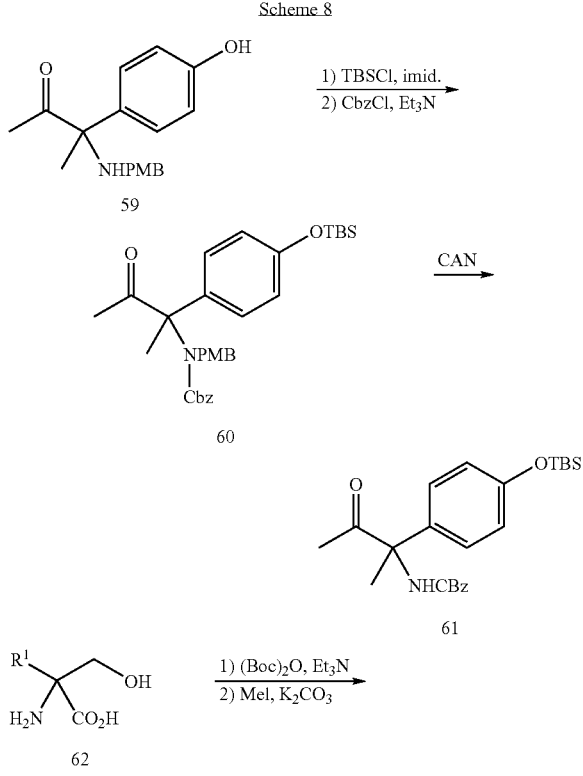

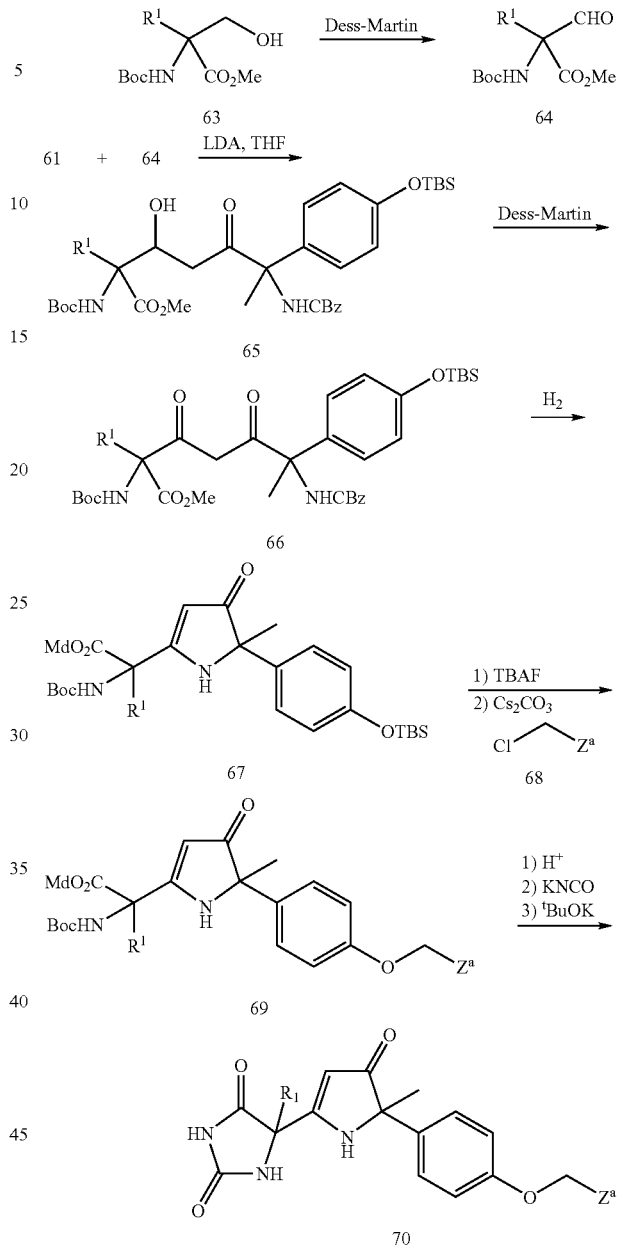

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "μg" for microgram, "mL" for milliliter or milliliters, "μL" for microliter(s), "mmol" for millimolar, "M" for molar, "mM" denotes millimolar, "nM" denotes nanomolar, "μM" denotes micromolar, "nm" for nanometer, "meq" for milliequivalent(s), "min" for minute or minute(s), "atm" for atmosphere, "conc." for concentrated, "MW" for molecular weight, "mp" for melting point, "rt" or "RT" for room temperature, "sat" or "sat'd" for saturated "¹H" for proton, "MHz" for megahertz, "MS" for mass spectroscopy, "NMR" for nuclear magnetic resonance spectroscopy, "rt" for room temperature, "tlc" for thin layer chromatography, "v/v" for volume to volume ratio, "ESI" for electrospray ionization mass spectroscopy, "HPLC" for high performance liquid chromatography, "MS" for mass spectrometry, "LC/MS" for liquid chromatography mass spectrometry, "NMR" for nuclear magnetic resonance spectroscopy, and "TLC" for thin layer chromatography. "Sigma" stands for the Sigma-Aldrich Corp. of St. Louis, Mo.

Solution ratio expresses a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

As used throughout the specification, the following abbreviations for chemical reagents apply:
HOAc or AcOH=acetic acid
Bn=benzyl
Bu=butyl
t-Bu=tertiary butyl
Boc=tert-butyl oxycarbonyl
DMF=dimethylformamide
DMSO=dimethyl sulfoxide
Et=ethyl
EtOH=ethanol
EtOAc=ethyl acetate
Me=methyl
MeOH=methanol
NaOAc=sodium actetate
OAc=acetate
Ph=phenyl
Pr=propyl
i-Pr=isopropyl
i-PrOH=isopropanol
TFA=trifluoroacetic acid
THF=tetrahydrofuran "α", "β", "R", "S", "E", and "Z" are stereochemical designations familiar to one skilled in the art. One stereoisomer of a compound of Formula (I) may display superior activity compared with the others. Thus, each stereoisomer of a compound of Formula (I) is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula (I) may also be directly synthesized using a chiral catalyst or a chiral ligand, e.g., Jacobsen, *E. Acc. Chem. Res.* 2000, 33, 421–431 or using other enantio- and diastereo-selective reactions and reagents known to one skilled in the art of asymmetric synthesis.

The following Examples have been prepared, isolated and characterized using the methods disclosed herein. The following Examples demonstrate a partial scope of the invention and are not meant to be limiting of the scope of the invention.

Example 1

5-{3-[4-(2-Methylquinolin-4-yl-methoxy)phenyl]-4,5-dihydroisoxazol-5-yl}imidazolidine-2,4-dione trifluoroacetate (1a): 4-Hydroxybenzaldehyde (9.23 g, 75.6 mmol), 4-Chloromethyl-2-methylquinoline (14.51 g, 1.05 eq), $K_2CO_3$ (19.9 g, 2 eq) and CH3CN (200 mL) were reflux for 3.5 h. The crude was then filtered and the filtrate was concentrated. The residue was dissolved in ethyl acetate (600 mL), washed with water (2×100 mL) and dried over $MgSO_4$. The solution was concentrated, triturated with ether and filtered. The product (20.46 g, 98%) was obtained as a pale yellow solid. MS Found: $(M^+H)^+=278$.

(1b): To a ethanol (200 mL) solution of the aldehyde (10.3 g, 37.18 mmol) from (1a) was added pyridine (7.35 mL, 2.5 eq) and hydroxylamine hydrochloride (5.16 g, 2 eq). The mixture was stirred at rt overnight. The crude was concentrated and the pure oxime (9.6 g, 88%) was obtained by flash column chromatography (10% MeOH—$CH_2Cl_2$). MS Found: $(M^+H)^+=293$.

(1c): Bleach (2 mL) was added to a $CH_2Cl_2$ (5 mL) solution of the oxime (200 mg, 0.684 mmol) from (1b) and acrolein (115 mg, 3 eq) and the mixture was stirred at rt for 2 h. The $CH_2Cl_2$ layer was then separated and concentrated. The 3-[4-(2-methylquinolin-4-yl-methoxy)phenyl]-4,5-dihydroisoxazole-5-carbaldehyde (140 mg, 59%) was obtained by reverse-phase preparative HPLC. MS Found: $(M^+H)^+=347$.

(1d): In a sealed tube, the aldehyde (140 mg, 0.404 mmol) from (1c), KCN (52.6 mg, 2 eq) and $(NH_4)_2CO_3$ (155 mg, 4 eq) were dissolved in ethanol (8 mL) and water (2 mL). The mixture was stirred at 90° C. for 1 h. The title hydantoin (fast diastereomer, 38 mg, 18%) was obtained by the reverse-phase preparative HPLC. MS Found: $(M^+H)^+=417$.

Example 2

5-{5-Methyl-3-[4-(2-methylquinolin-4-yl-methoxy)phenyl]4,5-dihydroisoxazol-5-yl}imidazolidine-2,4-dione trifluoroacetate (2a): Using a procedure analogous to reaction (1c), methylacrolein (96 mg, 2 eq) was reacted with the oxime from (1b) (200 mg, 0.684 mmol) to give the 5-methyl-3-[4-(2-methylquinolin-4-yl-methoxy)phenyl]4,5-dihydroisoxazole-5-carbaldehyde (200 mg, 81%). MS Found: $(M^+H)^+=361$.

(2b): Using a procedure analogous to reaction (1d), the aldehyde (200 mg, 0.555 mmol) from (2a) was converted to the title hydantoin (fast diastereomer, 51 mg, 17%). MS Found: $(M^+H)^+=431$.

Example 3

5-Methyl-5-{5-[4-(2-methyl-quinolin-4-ylmethoxy)-phenyl]-4,5-dihydro-isoxazol-3-yl}-imidazolidine-2,4-dione trifluoroacetate (3a): To a solution of but-3-en-2-ol (5.0 g, 69.34 mmol) in $CH_2Cl_2$ (100 mL) at 0° C. was added imidazole (5.66 g, 1.2 eq) and TBSCl (10.45 g, 1.0 eq). The reaction mixture was stirred at 0° C. to rt for 3 h. Solid was filtered off, the filtrate was concentrated and passed through a short silica gel column by eluting with hexane to give tert-butyl-dimethyl-(1-methyl-allyloxy)-silane (10.86 g, 85%) as a colorless oil.

(3b): To a dichloromethane (100 mL) solution of the olefin (10.23 g, 55.19 mmol) from (3a) at −78° C. was bubbled in $O_3$ until the solution turned blue. The reaction mixture was purged sequentially with $O_2$ and $N_2$ to colorless, then $Ph_3P$ (28.95 g, 2.0 eq) was added. The resulting mixture was stirred at rt for 2 h, concentrated, purified by flash column chromatography (5% ether-hexanes) to give 2-(tert-butyl-dimethyl-silanyloxy)-propionaldehyde (7.47 g, 72%) as a colorless oil.

(3c): To an ethyl acetate (100 ml) solution of aldehyde (2.7 g, 14.3 mmol) from (3b) at 0° C. was added a solution of hydroxylamine hydrochloride (2.5 g, 2.5 eq) and Et$_3$N (5.0 ml, 2.5 eq) in MeOH (25 ml). The reaction mixture was stirred at 0–5° C. for 4 h, filtered, the filtrate was washed with saturated NaHCO$_3$ and H$_2$O, dried and concentrated to give crude oxime product (2.30 g, 79%).

(3d): A mixture of 4-vinylphenol (10% wt. solution in propylene glycol) (1.25 g, 1.04 mmol), 4-Chloromethyl-2-methylquinoline (0.24 g, 1.2 eq), Cs$_2$CO$_3$ (0.85 g, 2.5 eq) and NaI (0.20 g, 1.2 eq) in DMSO (1 ml) was stirred at rt overnight. After work up, the residue was purified by flash column chromatography (40% ethyl acetate-hexanes) to give 2-methyl-4-(4-vinyl-phenoxymethyl)-quinoline (0.134 g, 46.8%) as a white solid. MS Found: (M$^+$H)$^+$=276.

(3e): To a stirred solution of NCS (46 mg, 1.0 eq) in anhydrous CHCl$_3$ (0.3 ml) and pyridine (1.7 μL) was added in the oxime (70 mg, 0.344 mmol) from (3c) in one portion at rt. After 15 min, the resulting mixture was added a solution of olefin (123 mg, 1.3 eq) in CHCl$_3$ (0.5 mL) and a solution of Et$_3$N (70 μL, 1.5 eq) in CHCl$_3$ (72 μL). After 16 h at rt, the reaction mixture was washed with brine, dried and concentrated to give crude 4-(4-{3-[1-(tert-butyl-dimethyl-silanyloxy)-ethyl]-4,5-dihydro-isoxazol-5-yl}phenoxymethyl)-2-methyl-quinoline which was used in next step without purification. MS Found: (M$^+$H)$^+$=276.

(3f): To a THF (2 mL) solution of crude product from (3e) at 0° C. was added a solution of Bu$_4$NF (0.35 mL, 1.0 M in THF, 1.03 eq) dropwise. The reaction mixture was stirred at this temperature for 30 min, then quenched with saturated NH$_4$Cl, extracted with ethyl acetate twice, the combined organic layers was dried and concentrated. 1-{5-[4-(2-Methyl-quinolin-4-ylmethoxy)-phenyl]-4,5-dihydro-isoxazol-3-yl}-ethanol (50 mg, 40% for two steps) was obtained as a white solid by flash column chromatography (40% ethyl acetate-hexanes, then 100% ethyl acetate). MS Found: (M$^+$H)$^+$=363.

(3g): To a CH$_2$Cl$_2$ (15 mL) solution of alcohol (50 mg, 0.138 mmol) from (3f) was added Dess-Martin reagent (58.5 mg, 1.0 eq). The reaction mixture was stirred for 1 h, solid was filtered off, the filtrate was concentrated and purified by flash column chromatography (60% ethyl acetate-hexanes) to give 1-{5-[4-(2-methyl-quinolin-4-ylmethoxy)-phenyl]-4,5-dihydro-isoxazol-3-yl}-ethanone (26.4 mg, 53%) as a clear glass solid. MS Found: (M$^+$H)$^+$=361.

(3h): The ketone (24 mg, 0.066 mmol) from (3g), KCN (4.3 mg, 1.0 eq), (NH$_4$)$_2$CO$_3$ (50.7 mg, 8.0 eq) were dissolved in ethanol (4 mL) and water (1 mL). The reaction mixture was heated at 75° C. overnight. The title hydantoin (12 mg, 33%) was obtained by reverse-phase preparative HPLC. MS Found: (M$^+$H)$^+$=431.

Example 4

5-Methyl-5-{5-methyl-5-[4-(2-methyl-quinolin-4-ylmethoxy)-phenyl]-4,5-dihydro-isoxazol-3-yl}-imidazolidine-2,4-dione trifluoroacetate (4a): Using a procedure analogous to reaction (3a), 1-(4-hydroxy-phenyl)-ethanone (1.36 g, 10 mmol) was converted to 1-[4-(tert-butyl-dimethyl-silanyloxy)-phenyl]-ethanone (2.35 g, 94%). $^1$H-NMR (300 MHz, CDCl$_3$): δ 6.883 (d, J=8.8 Hz, 2H), 6.875 (d, J=8.8 Hz, 2H), 2.558 (s, 3H), 0.989 (s, 9H), 0.234 (s, 6H).

(4b): To a stirred mixture of Ph$_3$P$^+$CH$_3$Br$^-$ (4.79 g, 2.0 eq) in THF (50 mL) at −20° C. was added n-BuLi (5.36 mL, 2.5 M in hexanes, 2.0 eq) dropwise. After stirring at this temperature for 30 min, a THF solution of ketone (1.68 g, 6.7 mmol) from reaction (4a) was added in one portion. The mixture was stirred at −20° C. for 20 min, then at rt for 2 h. The reaction was quenched with water, extracted with ether, dried and concentrated. tert-butyl-(4-isopropenyl-phenoxy)-dimethyl-silane (0.70 g, 42%) was obtained by flash column chromatography (5% ethyl acetate-hexanes). $^1$H-NMR (300 MHz, CDCl$_3$): δ 7.351 (d, J=8.8 Hz, 2H), 6.792 (d, J=8.8 Hz, 2H), 5.285 (d, J=0.7 Hz, 1H), 4.984 (t, J=1.5 Hz, 1H), 2.121 (d, J=0.8 Hz, 3H), 0.983 (s, 9H), 0.198 (s, 6H).

(4c): Using a procedure analogous to reaction (3e), the olefin (120 mg, 0.48 mmol) from (4b) and the oximes (100 mg, 1.02 eq) from (3c) were reacted to give the impure dihydroisoxazole (91.9 mg, 42%) after the crude was purified by flash column chromatography (5% ether-hexanes). MS Found: (M$^+$H)$^+$=450.

(4d): To a THF (2 mL) solution of bis-TBS protected dihydroisoxazole (90 mg, 0.20 mmol) from (4c) at 0° C. was added THF solution of TBAF (1M, 0.40 mL, 2.0 eq) and the mixture was stirred at this temperature for 30 min, then at rt for 45 min. The reaction was quenched with aqueous NH$_4$Cl, extracted with ethyl acetate, dried and concentrated. The residue was purified by flash column chromatography (40%–80% ethyl acetate-hexanes) to give 4-[3-(1-hydroxy-ethyl)-5-methyl-4,5-dihydro-isoxazol-5-yl]-phenol (34.2 mg, 77%).

(4e): Using a procedure analogous to reaction (3d), the phenol (34 mg, 0.15 mmol) from (4d) was coupled with 4-Chloromethyl-2-methylquinoline (29.4 mg, 1.0 eq) to give the 1-{5-methyl-5-[4-(2-methyl-quinolin-4-ylmethoxy)-phenyl]-4,5-dihydro-isoxazol-3-yl}-ethanol (46 mg, 81.6%) after the crude was purified by flash column chromatography (100% ethyl acetate). MS Found: (M$^+$H)$^+$=377.

(4f): Using a procedure analogous to reaction (3g), the alcohol (46 mg, 0.12 mmol) from (4e) was oxidized to ketone (33.3 mg, 72.9%). MS Found: (M$^+$H)$^+$=375.

(4g): Using a procedure analogous to reaction (3h), the ketone (32 mg, 0.0855 mmol) from (4f) was converted to the title hydantoin (20 mg, 41.8%) as a white powder after reverse-phase preparative HPLC purification. HR-MS Found: (M$^+$H)$^+$=445.1869.

Example 5

5-Methyl-5-{5-[4-(2-methyl-quinolin-4-ylmethoxy)-phenyl]-5-thiophen-2-yl-4,5-dihydro-isoxazol-3-yl}-imidazolidine-2,4-dione (5a): A solution of thiophene (0.60 mL, 7.5 mmol) in THF (15 mL) was cooled to −78° C., BuLi solution (2.5 M in hexanes, 3.0 mL, 7.5 mmol) was added dropwise, after 1 h at −78° C., a solution of 1-(4-hydroxy-phenyl)-ethanone (1.0 g, 7.34 mmol) was added. The slurry mixture was stirred at −78° C. for 2 h, then slowly warmed to rt. The reaction was quenched with saturated aqueous NH$_4$Cl, extracted with ethyl acetate, the extract was washed with brine, dried over MgSO$_4$ and concentrated to give yellow oil residue. To the above oil residue was added benzene (10 mL) and catalytic amount of TsOH. The mixture was heated with Dean-Stark trap for 15 min, then concentrated 4-(1-Thiophen-2-yl-vinyl)-phenol (170 mg, 11.5%) was obtained after flash column chromatography (20%–40% ethyl acetate-hexanes). MS Found: (M$^+$H)$^+$=203.

(5b): Using a procedure analogous to reaction (3e), the olefin (120 mg, 0.59 mmol) from (5a) and the oximes (100 mg, 0.5 mmol) from (3c) were reacted to give the dihydroisoxazole (41.5 mg, 20.5%) after the crude was purified by flash column chromatography (10%–20% ethyl acetate-hexanes). MS Found: $(M^+H)^+=404$.

(5c): To a THF (2 ml) solution of TBS protected dihydroisoxazole (41 mg, 0.10 mmol) from (5b) at 0° C. was added a solution of 1.0 M TBAF/THF (0.1 mL, 1.0 eq) and the mixture was stirred at this temperature for 30 min. The reaction was quenched with aqueous $NH_4Cl$, extracted with ethyl acetate, dried and concentrated. The residue was purified by flash column chromatography (40%–100% ethyl acetate-hexanes) to give 4-[3-(1-hydroxy-ethyl)-5-thiophen-2-yl-4,5-dihydro-isoxazol-5-yl]-phenol (10 mg, 34.6%) as a glass solid.

(5d): Using a procedure analogous to reaction (3d), the phenol (10 mg, 0.035 mmol) from (5c) was coupled with 4-chloromethyl-2-methylquinoline (6.7 mg, 1.0 eq) to give 1-{5-[4-(2-methyl-quinolin-4-ylmethoxy)-phenyl]-5-thiophen-2-yl-4,5-dihydro-isoxazol-3-yl}-ethanol (9.0 mg, 58%) after the crude was purified by flash column chromatography (80% ether-hexanes). MS Found: $(M^+H)^+=445$.

(5e): Using a procedure analogous to reaction (3g), the alcohol (9.0 mg, 0.02 mmol) from (5d) was oxidized to ketone (5.0 mg, 56%).

(5j): Using a procedure analogous to reaction (3h), the ketone (5.0 mg, 0.011 mmol) from (5e) was converted to the title hydantoin (4.1 mg, 70.8%) after the crude was purified by flash column chromatography (5%–10% MeOH—$CH_2Cl_2$. HR-MS Found: $(M^+H)^+=513.1601$.

Example 6

5-{5-Isopropyl-5-[4-(2-methylquinolin-4-yl-methoxy)phenyl]-4,5-dihydroisoxazol-3-yl}-5-methylimidazolidine-2,4-dione trifluoroacetate (6a): 1,2-dibromoethane (7.11 mL, 1.32 eq) was added to magnesium turnings (1.8235 g, 75 mmol, 1.2 eq) in dry THF (150 mL) at rt. The reaction was refluxed for 1 h then cooled to rt. This gave a freshly prepared $MgBr_2$ in THF as a white suspension. In a separate flask, a hexanes solution of butyllithium (2.5 M, 30 mL, 75 mmol, 1.2 eq) was added dropwise to a dry ether (200 mL) solution of 4-bromophenoxy-tert-butyldimethylsilane (17.96 g, 62.5 mmol) at −78° C. After 0.5 h, the prepared lithium reagent was cannulated into the $MgBr_2$ suspension at −78° C. After 0.5 h, the temperature was allowed to raise to −10° C. within 1 h hence the Grignard reagent was made.

(6b): A portion of the Grignard reagent (110 mL, 17.05 mmol) from (6a) was added to 3-methyl-2-butanone (1.469 g, 17.05 mmol) at 0° C. The reaction was allowed to slowly warm up to rt and stir overnight. It was quenched by adding water. The mixture was extracted with ethyl acetate, dried over $MgSO_4$ and concentrated to give crude (4.43 g) 2-[4-(tert-butyldimethylsilyloxy)phenyl]-3-methylbutan-2-ol as a pale yellow liquid.

(6c): To a benzene (20 mL) solution of the alcohol (1.7588 g, 5.97 mmol) from (6b) was added pTsOH (0.1136 g, 0.1 eq) and the mixture was warmed up to 50° C. for 6 h. A 1:1 mixture (1.2871 g) of tert-butyl[4-(1-isopropylvinyl)phenoxy]dimethylsilane and tert-butyl [4-(1,2-dimethylpropenyl)phenoxy]dimethylsilane was obtained as colorless oil by flash column chromatography (1% ethyl acetate-hexanes). MS Found: $(M^+H)^+=277$.

(6d): Using a procedure analogous to reaction (3e), the oximes (201 mg, 1.2 eq) from (3c) and the alkenes (227.6 mg, 0.825 mmol) from (6c) was reacted to give the impure dihydroisoxazole (151.3 mg) after the crude was purified once by flash column chromatography (3% ethyl acetate-hexanes). MS Found: $(M^+H)^+=478$.

(6e): To a $CH_2Cl_2$ solution of bis-TBS protected dihydroisoxazole (151.3 mg) from (6d) was added THF solution of TBAF (1 M, 1 mL) and the mixture was stirred at rt for 1 h. The pure 4-{3-[1-(tert-butyldimethylsilyloxy)ethyl]-5-isopropyl-4,5-dihydroisoxazol-5-yl}phenol (64.8 mg, 42% two-step) was obtained as pale yellow oil by flash column chromatography (40% ethyl acetate-hexanes). MS Found: $(M^+H)^+=364$.

(6f): Using a procedure analogous to reaction (3d), the phenol (64 mg, 0.176 mmol) from (6e) was coupled with 4-chloromethyl-2-methylquinoline (50 mg, 1.5 eq) to give the 4-(4-{3-[1-(tert-butyldimethylsilyloxy)ethyl]-5-isopropyl-4,5-dihydroisoxazol-5-yl}phenoxymethyl)-2-methylquinoline (46.5 mg, 51%). MS Found: $(M^+H)^+=519$.

(6g): Using a procedure analogous to reaction (3f), the TBS ether (46.5 mg, 0.09 mmol) from (6f) was deprotected to give 1-{5-isopropyl-5-[4-(2-methylquinolin-4-yl-methoxy)phenyl]-4,5-dihydroisoxazol-3-yl}ethanol (35.5 mg, 99%). MS Found: $(M^+H)^+=405$.

(6h): Using a procedure analogous to reaction (3g), the alcohol (23 mg, 0.057 mmol) from (6g) was oxidized to ketone (23 mg, 100%). MS Found: $(M^+H)^+=403$.

(6i): Using a procedure analogous to reaction (1d), the ketone (23 mg, 0.57 mmol) from (6h) was converted to the title hydantoin (14.4 mg, 54%) as a 1:1 diastereomeric mixture. MS Found: $(M^+H)^+=473$.

Example 7

{3-(4-Methyl-2,5-dioxo-imidazolidin-4-yl)-5-[4-(2-methyl-quinolin-4-ylmethoxy)-phenyl]-4,5-dihydro-isoxazol-5-ylmethyl}-carbamic acid tert-butyl ester trifluoroacetate (7a): To a solution of prop-2-ynylamine (5.50 g, 0.10 mmol), $Et_3N$ (14 ml, 1.5 eq) in $CH_2Cl_2$ (200 mL) was added $(Boc)_2O$ (21.8 g, 1.0 eq). The reaction mixture was stirred at rt for 2.5 h, then concentrated, the residue was passed through a silica gel pad, eluted with 20% ethyl acetate-hexanes (500 mL), the eluant was concentrated to give prop-2-ynyl-carbamic acid tert-butyl ester (15.40 g, 99.4%) as a crystalline solid.

(7b): To a solution of hexamethyldisilane (5.84 mL, 2.2 mmol) in dry HMPA (14.0 mL) at 0° C. under $N_2$ was added MeLi-LiBr complex in $Et_2O$ (1.5 M, 19.0 mL, 2.2 eq) dropwise. The mixture was stirred for 10 min, then cooled to −20° C., anhydrous THF (50 mL) was added, followed by CuCN (1.27 g, 1.1 eq), after 10 min, a solution of prop-2-ynyl-carbamic acid tert-butyl ester (2.0 g, 12.9 mmol) from (7a) was added. The resulting mixture was stirred at −20° C. for 2 h, quenched with saturated $NH_4Cl$ (20 mL), diluted with $Et_2O$ (50 mL) and stirred at rt overnight. The solid was filtered off, the organic layer was separated, and the aqueous layer was extracted with $Et_2O$, the combined organic layer was washed with water, dried and concentrated. (3-Trimethylsilanyl-allyl)-carbamic acid tert-butyl ester (1.70 g, 57%) was obtained as a colorless oil after the crude was purified by flash column chromatography (10% ether-hexanes).

(7c): Using a procedure analogous to reaction (1a), 4-iodophenol was reacted with 4-chloromethyl-2-methylquinoline to give the desired ether.

(7d): THF (1.5 mL), $Pd(OAc)_2$ (20 mg, 0.089 mmol, 8% eq) and 1,2-bis(diphenylphosphino)ethane (35.5 mg, 16% eq) were mixed under $N_2$, degassed and stirred to give orange yellow mixture. A premixed solution of (3-trimethylsilanylallyl)-carbamic acid tert-butyl ester (250 mg, 1.09 mmol) from (7b) and 4-(4-iodo-phenoxymethyl)-2-methyl-quinoline (410 mg, 1.0 eq) from (7c) in benzene (3 ml) was added. The resulting mixture was heated at 50° C. over the weekend, then cooled to rt, diluted with ether, washed with water, dried and concentrated. {2-[4-(2-Methyl-quinolin-4-ylmethoxy)-phenyl]-allyl}-carbamic acid tert-butyl ester (65 mg, 14.8%) was obtained after the crude was purified by flash column chromatography (20%–40% ethyl acetate-hexanes). MS Found: $(M^+H)^+=405$.

(7e): Using a procedure analogous to reaction (3e), the olefin (65 mg, 0.16 mmol) from (7d) and the oximes (32.7 mg, 1.0 eq) from (3c) were reacted to give the dihydroisoxazole (50 mg, 51.6%) after the crude was purified by flash column chromatography (20%–60% ethyl acetate-hexanes). MS Found: $(M^+H)^+=606$.

(7j): Using a procedure analogous to reaction (5c), the TBS-protected dihydroisoxazole (50 mg, 0.0825 mmol) was converted to alcohol (34.3 mg, 84.7%). MS Found: $(M^+H)^+=492$.

(7g): Using a procedure analogous to reaction (3g), the alcohol (34.3 mg, 0.07 mmol) from (7f) was oxidized to ketone (18.4 mg, 53.8%) as a glass solid. MS Found: $(M^+H)^+=490$.

(7h): Using a procedure analogous to reaction (3h), the ketone (17.0 mg, 0.035 mmol) from (7g) was converted to the title hydantoin (12.2 mg, 51.7%) after the crude was purified by reverse phase preparative HPLC. MS Found: $(M^+H)^+=560$.

Example 8

5-{5-Aminomethyl-5-[4-(2-methyl-quinolin-4-ylmethoxy)-phenyl]-4,5-dihydro-isoxazol-3-yl}-5-methyl-imidazolidine-2,4-dione di-trifluoroacetate The Boc-protected hydantoin (90 mg, 0.134 mmol) from (7h) was dissolved in TFA (0.2 mL)-$CH_2Cl_2$ (2 mL). The reaction mixture was stirred at rt for 1 h, concentrated to dryness. The residue was dissolved in water, lyophilized to give the title compound (79.5 mg, 86.6%) as TFA salt. MS Found: $(M^+H)^+=460$.

Example 9

N-{3-(4-Methyl-2,5-dioxo-imidazolidin-4-yl)-5-[4-(2-methyl-quinolin-4-ylmethoxy)-phenyl]-4,5-dihydro-isoxazol-5-ylmethyl}-acetamide trifluoroacetate To a suspension of amine TFA salt (10 mg, 0.0145 mmol) from Example 8 in $CH_2Cl_2$ (1.0 mL) was added $Et_3N$ (10 μL, 5.0 eq), the resulting clear solution was cooled to 0° C., AcCl (1.24 μL, 1.2 eq) was added. The reaction was stirred at 0° C. for 30 min, then at rt for 2 h, quenched with aqueous $NaHCO_3$, extracted with 10% MeOH—$CH_2Cl_2$. The extract was dried over $MgSO_4$, concentrated and purified by reverse phase preparative HPLC to give the title compound (5.9 mg, 66%). HR-MS Found: $(M^+H)^+=502.2083$.

Example 10

N-{3-(4-Methyl-2,5-dioxo-imidazolidin-4-yl)-5-[4-(2-methyl-quinolin-4-ylmethoxy)-phenyl]-4,5-dihydro-isoxazol-5-ylmethyl}-methanesulfonamide trifluoroacetate To a suspension of amine TFA salt (10 mg, 0.0145 mmol) from Example 8 in $CH_2Cl_2$ (1.0 mL) at 0° C. was added $Et_3N$ (6.1 μL, 3.0 eq), followed by MsCl (1.12 μL, 1.0 eq). The reaction was stirred for 2 h, then quenched with aqueous $NaHCO_3$. $CH_2Cl_2$ was removed, the residue was purified by reverse phase preparative HPLC to give the title compound (5.6 mg, 59.6%). HR-MS Found: $(M^+H)^+=538.1781$.

Example 11

N-{3-(4-Methyl-2,5-dioxo-imidazolidin-4-yl)-5-[4-(2-methyl-quinolin-4-ylmethoxy)-phenyl]-4,5-dihydro-isoxazol-5-ylmethyl}-isonicotinamide di-(trifluoroacetate)

To a solution of isonicotinic acid (1.8 mg, 1.0 eq) in DMF (1.0 ml) was added BOP (7.0 mg, 1.1 eq), amine TFA salt (10 mg, 0.0145 mmol) from Example 8 and $Et_3N$ (6.1 μL, 3 eq). The reaction was stirred at rt for 2 h. The title compound was obtained (9.4 mg, 81.7%) as a white powder after purification by reverse-phase preparative HPLC. HR-MS Found: $(M^+H)^+=565.2204$.

Example 12

N-{3-(4-Methyl-2,5-dioxo-imidazolidin-4-yl)-5-[4-(2-methyl-quinolin-4-ylmethoxy)-phenyl]-4,5-dihydro-isoxazol-5-ylmethyl}-benzamide trifluoroacetate To a suspension of amine TFA salt (10 mg, 0.0145 mmol) from Example 8 in $CH_2Cl_2$ (1.0 mL) at 0° C. was added $Et_3N$ (6.1 μL, 3.0 eq), followed by benzoyl chloride (1.68 μL, 1.0 eq). The reaction was stirred for 2 h, then quenched with aqueous $NaHCO_3$. $CH_2Cl_2$ was removed, the residue was purified by reverse-phase preparative HPLC to give the title compound (7.3 mg, 74.5%) as a white powder. HR-MS Found: $(M^+H)^+=564.2244$.

Example 13

5-Methyl-5-{5-[4-(2-methyl-quinolin-4-ylmethoxy)-phenyl]-5-morpholin-4-ylmethyl-4,5-dihydro-isoxazol-3-yl}-imidazolidine-2,4-dione di-trifluoroacetate (13a): To a dry THF (25 mL) solution of ketone (5.0 g, 20 mmol) from reaction (4a) was added phenyltrimethylammonium tribromide (7.50 g, 1.0 eq) in portions. The reaction was stirred at rt for 1 h, quenched with water (100 mL), and extracted with ether. The ether extract was dried, concentrated and purified by flash column chromatography (5%–10% ether-hexanes) to give 2-bromo-1-[4-(tert-butyl-dimethyl-silanyloxy)-phenyl]-ethanone (6.14 g, 84%) as colorless oil. MS Found: $(M^+H)^+=329$, $(M^+H^+2)^+=331$.

(13b): To an $CH_3CN$ (10 ml) solution of bromoketone (1.0 g, 3.04 mmol) from reaction (13a) was added morpholine (0.27 mL, 1.02 eq) followed by $Et_3N$ (0.42 mL, 1.0 eq). The reaction was stirred at rt for 10 min, quenched with $H_2O$, extracted with ethyl acetate. 1-[4-(tert-Butyl-dimethyl-silanyloxy)-phenyl]-2-morpholin-4-yl-ethanone (0.82 g, 84%) was obtained after the crude was purified by flash column chromatography (50% ethyl acetate-hexanes).

(13c): Using a procedure analogous to reaction (4b), the ketone (0.80 g, 2.38 mmol) from (13b) was converted to olefin (70 mg, 8.8%) which was purified by flash column chromatography (20%–40% ethyl acetate-hexanes).

(13d): Using a procedure analogous to reaction (3e), the olefin (60 mg, 0.18 mmol) from (13c) and the oximes (40.7 mg, 1.1 eq) from (3c) were reacted to give the impure dihydroisoxazole (76 mg, 78.9%) after the crude was purified by flash column chromatography (10%–20% ethyl acetate-hexanes).

(13e): Using a procedure analogous to reaction (4d), the bis-TBS ether (76 mg, 0.14 mmol) from (13d) was deprotected to give 4-[3-(1-hydroxy-ethyl)-5-morpholin-4-ylmethyl-4,5-dihydro-isoxazol-5-yl]-phenol (20 mg, 45%) after the crude was purified by flash column chromatography (60%–100% ethyl acetate-hexanes). MS Found: $(M^+H)^+$ =307.

(13f): Using a procedure analogous to reaction (3d), the phenol (20 mg, 0.065 mmol) from (13e) was coupled with 4-chloromethyl-2-methylquinoline (12.5 mg, 1.0 eq) to give 1-{5-[4-(2-methyl-quinolin-4-ylmethoxy)-phenyl]-5-morpholin-4-ylmethyl-4,5-dihydro-isoxazol-3-yl}-ethanol (20 mg, 67%) as a glass solid after the crude was purified by flash column chromatography (0%–5% MeOH-ethyl acetate). MS Found: $(M^+H)^+$=462.

(13g): Using a procedure analogous to reaction (3g), the alcohol (20 mg, 0.043 mmol) from (13f) was oxidized to ketone, which was used in next step without purification. MS Found: $(M^+H)^+$=460.

(13h): Using a procedure analogous to reaction (3h), the crude ketone from (13g) was converted to the title hydantoin (3.0 mg, 9.2% for 2 steps) after reverse-phase preparative HPLC purification. HR-MS Found: $(M^+H)^+$=530.2417.

Example 14

5-{5-Hydroxymethyl-5-[4-(2-methyl-quinolin-4-ylmethoxy)-phenyl]-4,5-dihydro-isoxazol-3-yl}-5-methyl-imidazolidine-2,4-dione trifluoroacetate (14a): To a stirred mixture of $SeO_2$ (22.3 mg, 5% eq) and t-BuOOH (2.5 ml, 5–6 M in decane, 3.5 eq) in $CH_2Cl_2$ (10 mL) was added a solution of olefin (1.0 g, 4.0 mmol) from reaction (4b) at rt. The mixture was stirred at rt for 4 days, diluted with ether (25 ml) and washed successively with 1N KOH (2×10 ml), water and brine, dried over $MgSO_4$, concentrated. 2-[4-(tert-Butyl-dimethyl-silanyloxy)-phenyl]-prop-2-en-1-ol (0.50 g, 47%) was obtained as pale yellow oil after the crude was purified by flash column chromatography (20%–40% ethyl acetate-hexanes). MS Found: $(M^+H)^+$=265.

(14b): Using a procedure analogous to reaction (3e), the olefin (264 mg, 1.0 mmol) from (14a) and the oximes (230 mg, 1.13 eq) from (3c) were reacted to give the dihydroisoxazole (300 mg, 64%) after the crude was purified by flash column chromatography (10%–20% ethyl acetate-hexanes). MS Found: $(M^+H)^+$=466.

(14c): To a $CH_2Cl_2$ (4 ml) solution of alcohol (300 mg, 0.644 mmol) from (14b) at 0° C. was added pyridine (0.10 mL, 2 eq) and AcCl (45.6 μL, 1.0 eq). The mixture was stirred at 0° C. for 45 min, after regular work up, the residue was purified by flash column chromatography (5%–20% ethyl acetate-hexanes) to give acetic acid 3-[1-(tert-butyl-dimethyl-silanyloxy)-ethyl]-5-[4-(tert-butyl-dimethyl-silanyloxy)-phenyl]-4,5-dihydro-isoxazol-5-ylmethyl ester (230 mg, 70%). MS Found: $(M^+H)^+$=508.

(14d): Using a procedure analogous to reaction (4d), the bis-TBS ether (230 mg, 0.45 mmol) from (14c) was deprotected to give acetic acid 3-(1-hydroxy-ethyl)-5-(4-hydroxy-phenyl)-4,5-dihydro-isoxazol-5-ylmethyl ester (90 mg, 72%) after the crude was purified by flash column chromatography (100% ethyl acetate). MS Found: $(M-H)^-$=278.

(14e): Using a procedure analogous to reaction (3d), the phenol (90 mg, 0.32 mmol) from (14e) was coupled with 4-chloromethyl-2-methylquinoline (62 mg, 1.0 eq) to give acetic acid 3-(1-hydroxy-ethyl)-5-[4-(2-methyl-quinolin-4-ylmethoxy)-phenyl]-4,5-dihydro-isoxazol-5-ylmethyl ester (82.3 mg, 59%) as a solid after the crude was purified by flash column chromatography (80% ether-hexanes, 100% ethyl acetate, then 5% MeOH-ethyl acetate). MS Found: $(M^+H)^+$=435.

(14f): Using a procedure analogous to reaction (3g), the alcohol (80 mg, 0.189 mmol) from (14e) was oxidized to acetic acid 3-acetyl-5-[4-(2-methyl-quinolin-4-ylmethoxy)-phenyl]-4,5-dihydro-isoxazol-5-ylmethyl ester (53.4 mg, 66.8%) as a glass solid after the crude was purified by flash column chromatography (60%–80% ethyl acetate-hexanes). MS Found: $(M^+H)^+$=433.

(14g): Using a procedure analogous to reaction (3h), the ketone (50 mg, 0.1156 mmol) from (14f) was converted to the title hydantoin (12 mg, 18%) after reverse-phase preparative HPLC purification. HR-MS Found: $(M^+H)^+$=461.

Example 15

(±)5-Methyl-5-{5-[4-(2-methylquinolin-4-yl-methoxy)phenyl]-isoxazol-3-yl-methyl}imidazolidine-2,4-dione trifluoroacetate (15a): Using a procedure analogous to reaction (3a), 4-penten-2-ol (15.4 g, 0.179 mol) was converted to TBS ether (39.12 g, 100%) as an oil. MS Found: $(M^+H)^+$=201.

(15b): Using a procedure analogous to reaction (3b) except that the intermediate ozonide was quenched by polymer bonded $PPh_3$ (Synth. Commun. 1986, 16, 667–672), the TBS ether (23.85 g, 119 mmol) from (15a) was converted to aldehyde as an oil (19.423 g, 81%).

(15c): Using a procedure analogous to reaction (3c), the aldehyde (1,66 g, 8.22 mmol) from (15b) was converted to 1:1 mixture of Z/E oximes (1.66 g, 93%) as an oil.

(15d): To a $CH_3CN$ (200 mL) solution of 4-chloromethyl-2-methylquinoline (10.22 g, 53.3 mmol) and 4-iodophenol (11.98 g, 1.02 eq) was added $K_2CO_3$. The suspension was heated to reflux for 6 h. The mixture was then filtered through Celite® while the solution was still hot. The 4-(4-iodo-phenoxymethyl)-2-methylquinoline (20 g, 100%) was obtained as fine crystals after recrystalization in $CH_3CN$.

(15e): To a dry, degassed benzene (100 mL) solution of the iodide (3.97 g, 10.59 mmol) from (15d) was added $Pd(PPh_3)_4$ (2.45 g, 0.2 eq), CuI (2.02 g, 1 eq), trimethylsilyl acetylene (4.49 g, 10 eq) and TEA (3 mL, 2 eq). The mixture was warmed up to 40° C. overnight. The pure 2-methyl-4-(4-trimethylsilylethynylphenoxymethyl)quinoline (3.27 g, 90%) was obtained by flash column chromatography (40% ethyl acetate-hexanes) as a white solid. MS Found: $(M^+H)^+$=346.

(15j): Using a procedure analogous to reaction (3f), the TMS protected alkyne from (15e) (3.27 g, 9.48 mmol) was deprotected to give the pure 4-(4-ethynylphenoxymethyl)-2-methylquinoline (2.39 g, 92%) as a white solid. MS Found: $(M^+H)^+$=274.

(15g): To a DMF (30 mL) solution of the oxime (1.28 g, 5.9 mmol) from (15c) at 0° C. was added a DMF (20 mL) solution of NBS (1.57 g, 1.5 eq). The resulting golden yellow solution was continued to stir at 0° C. for 1 h. A DMF (10 mL) solution of TEA (1.233 mL, 1.5 eq) and the alkyne (1.61 g, 1 eq) from (15f) was then added dropwise at 0° C. The golden color faded with the addition. The ice bath was removed and the reaction was allowed to stir at rt overnight. The mixture was then poured into water (200 mL), extracted with ethyl acetate (2×50 mL), washed with water (100 mL), concentrated. A mixture (1.14 g) of 4-(4-{3-[2-(tert-butyldimethylsilyloxy)propyl]isoxazol-5-yl}phenoxymethyl)-2-methylquinoline and the starting alkyne was obtained after the crude was purified by flash column chromatography (30% ethyl acetate-hexanes). MS Found: (M+H)+=489.

(15h): To a CH$_2$Cl$_2$ (10 mL) solution of the mixture (1.14 g) from (15g) was added a THF (4 mL) solution of TBAF (1 M) and 4 A molecular sieve (2.4 g). The mixture was stirred at 40° C. overnight. It was then diluted with ethyl acetate (100 mL) and filtered through Celite®. The filtrate was washed with water (2×100 mL) and dried over Na$_2$SO$_4$. The pure 1-{5-[4-(2-methylquinolin-4-yl-methoxy)phenyl]isoxazol-3-yl}-propan-2-ol (0.38 g, 20% two-step) was obtained by flash column chromatography (ethyl acetate) as a white solid. MS Found: (M+H)+=375.

(15i): Using a procedure analogous to reaction (3g), the alcohol (380 mg, 1.016 mmol) from (15h) was oxidized to ketone (340 mg, 90%). MS Found: (M+H)+=373.

(15j): Using a procedure analogous to reaction (1d), the ketone (0.26 g, 0.70 mmol) from (15i) was converted to the title hydantoin (0.28 g, 73%). MS Found: (M+H)+=443.

Table 1 below provides representative examples, the synthesis of which is described above, of the compounds in the present invention.

TABLE 1

(Ia)

| Ex | R$^1$ | L | Z$^0$ | MS (M + 1) |
|---|---|---|---|---|
| 1 | H | bond | isoxazoline (O—N, 5-sub, 3-sub) | 547.5 |
| 2 | H | bond | isoxazoline with Me | 594.5 |
| 3 | Me | bond | isoxazoline (N—O) | 610.5 |
| 4 | Me | bond | isoxazoline with Me | 516.4 |
| 5 | Me | bond | isoxazoline with thienyl | 492.3 |
| 6 | Me | bond | isoxazoline with i-Pr | 448.5 |

TABLE 1-continued
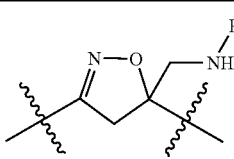
(Ia)
| Ex | R¹ | L | Z⁰ | MS (M + 1) |
|----|----|----|----|----|
| 7 | Me | bond | 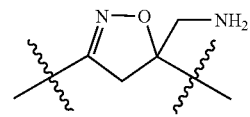 isoxazoline-CH₂-NH-Boc | 448.5 |
| 8 | Me | bond | isoxazoline-CH₂-NH₂ | 534.3 |
| 9 | Me | bond | isoxazoline-CH₂-NH-COMe | 506.3 |
| 10 | Me | bond | isoxazoline-CH₂-NH-SO₂Me | 547.5 |
| 11 | Me | bond | isoxazoline-CH₂-NH-C(O)-4-pyridyl | 547.3 |
| 12 | Me | bond | isoxazoline-CH₂-NH-C(O)-3-pyridyl | 492.3 |
| 13 | Me | bond | isoxazoline-CH₂-morpholino | 449.4 |

TABLE 1-continued

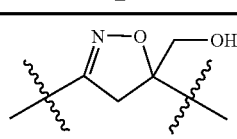

(Ia)

| Ex | R¹ | L | Z⁰ | MS (M + 1) |
|---|---|---|---|---|
| 14 | Me | bond | (N—O isoxazoline with —CH₂—OH) | 483.4 |
| 15 | Me | —CH₂— | (N—O isoxazole) | 497.0 |

Utility

The compounds of the present invention are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of the present invention are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, Cancer and Metastasis Reviews, 1990, 9, 289–303). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TACE and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

The compounds of the present invention can be administered alone or in combination with one or more additional anti-inflammatory agents. These agents include, but are not limited to, selective COX-2 inhibitors, interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denotes agents that selectively inhibit COX-2 function. Such agents include, but are not limited to, celecoxib (Celebrex®), rofecoxib (Vioxx®), meloxicam (Movicox®), etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel®), infliximab (Remicade®), adalimumab (D2E7), CDP-571 (Humicade®), and CDP-870.

Other anti-inflammatory agents that may be used in combination with the compounds of this invention, include, but are not limited to, methotrexate, interleukin-1 antagonists (e.g., anakinra (Kineret®)), dihydroorotate synthase inhibitors (e.g., leflunomide (Arava®)), and p38 MAP kinase inhibitors.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

A compound is considered to be active if it has an $IC_{50}$ or $K_i$ value of less than about 10 µM for the inhibition of a desired MP. Preferred compounds of the present invention have $K_i$'s or $IC_{50}$'s of ≦1 µM. More preferred compounds of the present invention have $K_i$'s or $IC_{50}$'s of ≦0.1 µM. Even more preferred compounds of the present invention have $K_i$'s or $IC_{50}$'s of ≦0.01 µM. Still more preferred compounds of the present invention have $K_i$'s or $IC_{50}$'s of ≦0.001 µM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et al. *Trans. Ortho. Res. Soc.* 1995, 20, 341). Therefore, in order to accumulate BNC aggrecanase in culture media, cartilage is first depleted of endogenous aggrecan by stimulation with 500 mg/ml human recombinant IL-β, for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al. *Biochem J.* 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a $K_m$ of 1.5±/−0.35 µM for aggrecanase.

To evaluate inhibition of aggrecanase, compounds are prepared as 10 mM stocks in DMSO, water or other solvents and diluted to appropriate concentrations in water. Drug (50 mL) is added to 50 µL of aggrecanase-containing media and 50 µL of 2 mg/mL aggrecan substrate and brought to a final volume of 200 µL in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 µg GAG) for 2 hr at 37° C. and then with keratanase (0.1 units/10 µg GAG) and keratanase II (0.002 units/10 µg GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 µL of Tris glycine SDS sample buffer (Novex®) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

TNF PBMC Assay

Human peripheral blood mononuclear cells (PBMC) were obtained from normal donor blood by leukophoresis and isolated by Ficoll-Paque density separation. PBMCs were suspended in 0.5 mL RPMI 1640 with no serum at $2 \times 10^6$ cells/mL in 96 well polystyrene plates. Cells were preincubated 10 minutes with compound, then stimulated with 1 μg/mL LPS (Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 μL of blood is plated directly into sterile polypropylene tubes. Compounds are diluted in DMSO/serum free media and added to the blood samples so the final concentration of compounds are 50, 10, 5, 1, 0.5, 0.1, and 0.01 μM. The final concentration of DMSO does not exceed 0.5%. Compounds are preincubated for 15 minutes before the addition of 100 μg/mL LPS. Plates are incubated for 5 hours in an atmosphere of 5% $CO_2$ in air. At the end of 5 hours, 750 μL of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

TNF Induction in Mice

Test compounds are administered to mice either I.P. or P.O. at time zero. Immediately following compound administration, mice receive an I.P. injection of 20 mg of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 μM in all assays. Initial velocities, in the presence or absence of inhibitor, were measured as slopes of the linear portion of the product progress curves. $IC_{50}$ values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibition, the $IC_{50}$ values were converted to $K_i$ values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of an inflammatory disorder (as defined previously). In another embodiment, the package insert states that the pharmaceutical composition can be used in combination (as defined previously) with a second therapeutic agent to treat an inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences*.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 mg to about 100 mg of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, a standard reference text in this field.

The compounds of the present invention may be administered in combination with a second therapeutic agent, especially non-steroidal anti-inflammatory drugs (NSAID's). The compound of the present invention and such second therapeutic agent can be administered separately or as a physical combination in a single dosage unit, in any dosage form and by various routes of administration, as described above.

The compound of the present invention may be formulated together with the second therapeutic agent in a single dosage unit (that is, combined together in one capsule, tablet, powder, or liquid, etc.). When the compound of the present invention and the second therapeutic agent are not formulated together in a single dosage unit, the compound of the present invention and the second therapeutic agent may be administered essentially at the same time, or in any order; for example the compound of the present invention may be administered first, followed by administration of the second agent. When not administered at the same time, preferably the administration of the compound of the present invention and the second therapeutic agent occurs less than about one hour apart, more preferably less than about 5 to 30 minutes apart.

Preferably the route of administration of the compound of the present invention is oral. Although it is preferable that the compound of the present invention and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of the present invention when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of the present invention. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:
1. A compound of Formula (I):

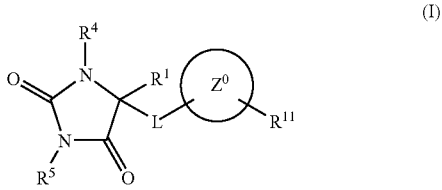

or a stereoisomer or pharmaceutically acceptable salt or solvate form thereof, wherein:

$R^1$ is Q, —$C_{1-6}$ alkylene-Q, —$C_{2-6}$ alkynylene-Q, —$C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rOC(O)(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rOC(O)O(CR^aR^{a1})_s$-Q, —$(CR^aR^{a1})_rOC(O)NR^a(CR^aR^{a1})_s$-Q, —$(CR^aR^{a1})_rNR^aC(O)O(CR^aR^{a1})_s$-Q, —$(CR^aR^{a1})_rNR^aC(O)NR^a(CR^aR^{a1})_s$-Q, —$(CR^aR^{a1})_rS(CR^aR^{a1})_s$-Q, —$(CR^aR^{a1})_rS(O)(CR^aR^{a1})_s$-Q, —$(CR^aR^{a1})_rS(O)_2(CR^aR^{a1})_s$-Q, —$(CR^aR^{a1})_rSO_2NR^a(CR^aR^{a1})_s$-Q, —$(CR^aR^{a1})_rNR^aSO_2(CR^aR^{a1})_s$-Q, or —$(CR^aR^{a1})_rNR^aSO_2NR^a(CR^aR^{a1})_s$-Q;

L is a bond, CO or $(CR^2R^3)_m$;

$R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_rNR^aC(O)(CR^aR^{a1})_s$-$Q^1$, —$(CR^aR^{a1})_rOC(O)O(CR^aR^{a1})_s$-$Q^1$, —$(CR^aR^{a1})_rOC(O)NR^a(CR^aR^{a1})_s$-$Q^1$, —$(CR^aR^{a1})_rNR^aC(O)NR^a(CR^aR^{a1})_s$-$Q^1$, —$(CR^aR^{a1}_2)_rS(O)_p(CR^aR^{a1})_s$-$Q^1$, —$(CR^aR^{a1})_rSO_2NR^a(CR^aR^{a1})_s$-$Q^1$, —$(CR^aR^{a1})_rNR^aSO_2(CR^aR^{a1})_s$-$Q^1$, or —$(CR^aR^{a1})_rNR^aSO_2NR^a(CR^aR^{a1})_s$-$Q^1$;

$R^3$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rNR^aC(O)(CR^aR^{a1})_s$-Q, —$(CR^aR^{a1})_rS(O)_p(CR^aR^{a1})_s$-Q, —$(CR^aR^{a1})_rSO_2NR^a(CR^aR^{a1})_s$-Q, or —$(CR^aR^{a1})_rNR^aSO_2(CR^aR^{a1})_s$-Q;

Q is, independently at each occurrence, H, $CHF_2$, $CH_2F$, $CF_3$, a $C_{3-13}$ carbocycle substituted with 0–5 $R^d$ or a 5–14 membered heterocycle consisting of carbon atoms and 1–4 heteroatoms selected from the group consisting of N, O, and $S(O)_p$, and substituted with 0–5 $R^d$;

$Q^1$ is, independently at each occurrence, H, a $C_{3-13}$ carbocycle substituted with 0–5 $R^d$ or a 5–14 membered heterocycle consisting of carbon atoms and 1–4 heteroatoms selected from the group consisting of N, $NR^7$, O, and $S(O)_p$, and substituted with 0–5 $R^d$;

ring $Z^0$ is a 5–7 membered heterocycle consisting of carbon atoms, 0–2 carbonyls, and 0–3 ring heteroatoms selected from O, N, $NR^7$, and $S(O)_p$;

provided that L and $R^{11}$ are not attached to the same ring atom or adjacent ring atoms of ring $Z^0$;

ring $Z^0$ is substituted with 0–2 $R^6$ and contains 0–3 ring double bonds;

$R^{11}$ is —W—U—X—Y-Z-$U^a$—$X^a$—$Y^a$-$Z^a$;

W is a bond, $(CR^aR^{a1})_m$, $C_{2-3}$ alkenylene, or $C_{2-3}$ alkynylene;

U is absent or is O, $NR^{a1}$, C(O), $CR^a(OH)$, C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_pNR^{a1}$, $NR^{a1}S(O)_p$, or $NR^{a1}SO_2NR^{a1}$;

X is absent or is $C_{1-3}$ alkylene, $C_{2-3}$ alkenylene, or $C_{2-3}$ alkynylene;

Y is absent or is O, $NR^{a1}$, $S(O)_p$, or C(O);

Z is a $C_{3-13}$ carbocycle substituted with 0–5 $R^b$ or a 5–14 membered heterocycle consisting of carbon atoms and 1–4 heteroatoms selected from the group consisting of N, O, and $S(O)_p$, and substituted with 0–5 $R^b$;

$U^a$ is absent or is O, $NR^{a1}$, C(O), $CR^a(OH)$, C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_pNR^{a1}$, $NR^{a1}S(O)_p$, or $NR^{a1}SO_2NR^{a1}$;

$X^a$ is absent or is $C_{1-10}$ alkylene, $C_{2-10}$ alkenylene, or $C_{2-10}$ alkynylene;

$Y^a$ is absent or is O, $NR^{a1}$, $S(O)_p$, or C(O);

$Z^a$ is a $C_{3-13}$ carbocycle substituted with 0–5 $R^c$ or a 5–14 membered heterocycle consisting of carbon atoms and 1–4 heteroatoms selected from the group consisting of N, O, and $S(O)_p$, and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^a$ is, independently at each occurrence, H, $C_{1-6}$ alkyl, phenyl, or benzyl;

$R^{a1}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$-3–8 membered carbocycle or heterocycle consisting of carbon atoms and 0–2 ring heteroatoms selected from N, $NR^{a2}$, O, and $S(O)_p$, and substituted with 0–3 $R^{c1}$;

alternatively, $R^a$ and $R^{a1}$ when attached to a nitrogen, together with the nitrogen to which they are attached, combine to form a 5 or 6 membered heterocycle consisting of carbon atoms and 0–1 additional heteroatoms selected from N, $NR^{a2}$, O, and $S(O)_p$;

$R^{a2}$ is, independently at each occurrence, $C_{1-4}$ alkyl, phenyl, or benzyl;

$R^{a3}$, independently at each occurrence, H, $C_{1-6}$ alkyl substituted with $R^{c1}$, $C_{2-6}$ alkenyl substituted with 0–1 $R^{c1}$, $C_{2-6}$ alkynyl substituted with 0–1 $R^{c1}$, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

$R^b$, independently at each occurrence, $C_{1-6}$ alkyl substituted with 0–1 $R^{c1}$, —$OR^a$, —$SR^a$, Cl, F, Br, I, =O, —CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, $CF_3$, —$CF_2CF_3$, $CHF_2$, $CH_2F$, or phenyl;

$R^c$ is, independently at each occurrence, H, Cl, F, Br, I, =O, —CN, $NO_2$, $CF_3$, —$CF_2CF_3$, $CH_2F$, $CHF_2$, —$(CR^aR^{a1})_rOR^a$, —$(CR^aR^{a1})_rNR^aR^{a1}$, —$(CR^aR^{a1})_rC(=NCN)NR^aR^{a1}$, —$(CR^aR^{a1})_rC(=NR^a)NR^aR^{a1}$, —(CR$^a$R$^{a1}$)$_r$C(=NOR$^a$)NR$^a$R$^{a1}$, —(CR$^a$R$^{a1}$)$_r$C(O)NR$^a$OH, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$C(S)NR$^a$R$^{a1}$, —(CR$^a$R$^{a1}$)$_r$OC(O)NR$^a$R$^{a1}$, —(CR$^a$R$^{a1}$)$_r$NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —(CR$^a$R$^{a1}$)$_r$NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–14 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^{c1}$ is, independently at each occurrence, H, C$_{1-4}$ alkyl, —OR$^a$, Cl, F, Br, I, =O, CF$_3$, —CN, NO$_2$, —C(O)R$^a$, —C(O)OR$^a$, —C(O)NR$^a$R$^a$, or —S(O)$_p$R$^a$;

R$^d$ is, independently at each occurrence, C$_{1-6}$ alkyl, —OR$^a$, Cl, F, Br, I, =O, —CN, NO$_2$, —NR$^a$R$^{a1}$, —C(O)R$^a$, —C(O)OR$^a$, —C(O)NR$^a$R$^{a1}$, —C(S)NR$^a$R$^{a1}$, —NR$^a$C(O)NR$^a$R$^{a1}$, —OC(O)NR$^a$R$^{a1}$, —NR$^a$C(O)OR$^a$, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, —S(O)$_p$R$^{a3}$, CF$_3$, —CF$_2$CF$_3$, C$_{3-10}$ carbocycle, or a 5–14 membered heterocycle consisting of carbon atoms and 1–4 heteroatoms selected from the group consisting of N, O, and S(O)$_p$;

R$^e$ is, independently at each occurrence, H, C$_{1-6}$ alkyl, C$_{1-6}$ alkoxy, phenoxy, benzoxy, C$_{3-10}$ carbocycle substituted with 0–2 R$^{c1}$, or a 5–10 membered heterocycle consisting of carbon atoms and 1–4 heteroatoms selected from the group consisting of N, O, and S(O)$_p$, and substituted with 0–2 R$^{c1}$;

R$^4$ is H, C$_{1-4}$ alkyl, C$_{2-4}$ alkenyl, or C$_{2-4}$ alkynyl;

R$^5$ is H, C$_{1-4}$ alkyl, C$_{2-4}$ alkenyl, or C$_{2-4}$ alkynyl;

R$^6$ is, independently at each occurrence, H, Cl, F, Br, I, =O, —CN, NO$_2$, CF$_3$, —CF$_2$CF$_3$, —(CR$^a$R$^{a1}$)$_r$OR$^a$, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)R$^a$, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$C(S)NR$^a$R$^{a1}$, —(CR$^a$R$^{a1}$)$_r$OC(O)NR$^a$R$^{a1}$, —(CR$^a$R$^{a1}$)$_r$NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —(CR$^a$R$^{a1}$)$_r$NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

R$^7$ is, independently at each occurrence, H, —(CR$^a$R$^{a1}$)$_t$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_t$NR$^a$C(O)R$^{a1}$, —(CR$^a$R$^{a1}$)$_r$C(S)NR$^a$R$^{a1}$, —(CR$^a$R$^{a1}$)$_t$OC(O)NR$^a$R$^{a1}$, —(CR$^a$R$^{a1}$)$_r$NR$^a$C(O)OR$^{a1}$, —(CR$^a$R$^{a1}$)$_t$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_t$NR$^a$SO$_2$R$^{a3}$, —(CR$^a$R$^{a1}$)$_t$NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$_d$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

m, at each occurrence, is selected from 1, 2 and 3;
p, at each occurrence, is selected from 0, 1, and 2;
r, at each occurrence, is selected from 0, 1, 2, 3, and 4;
s, at each occurrence, is selected from 0, 1, 2, 3, and 4; and
t, at each occurrence, is selected from 1, 2, 3, and 4.

2. A compound according to claim 1, wherein:

R$^1$ is Q, —C$_{1-6}$ alkylene-Q, —C$_{2-6}$ alkenylene-Q, —C$_{2-6}$ alkynylene-Q, —(CR$^a$R$^{a1}$)$_t$O(CR$^a$R$^{a1}$)$_s$-Q, —(CR$^a$R$^{a1}$)$_t$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$OC(O)(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_t$NR$^a$C(O)(CR$^a$R$^{a1}$)$_s$-Q, —(CR$^a$R$^{a1}$)$_t$S(CR$^a$R$^{a1}$)$_s$-Q, —(CR$^a$R$^{a1}$)$_r$S(O)(CR$^a$R$^{a1}$)$_s$-Q, —(CR$^a$R$^{a1}$)$_r$S(O)$_2$(CR$^a$R$^{a1}$)$_s$-Q, —(CR$^a$R$^{a1}$)$_r$SO$_2$NR$^a$(CR$^a$R$^{a1}$)$_s$-Q, or —(CR$^a$R$^{a1}$)$_r$NR$^a$SO$_2$(CR$^a$R$^{a1}$)$_s$-Q;

R$^2$ is Q$^1$, —C$_{1-6}$ alkylene-Q$^1$, —C$_{2-6}$ alkenylene-Q$^1$, —C$_{2-6}$ alkynylene-Q$^1$, —(CR$^a$R$^{a1}$)$_r$O(CR$^a$R$^{a1}$)$_s$-Q$^1$, —(CR$^a$R$^{a1}$)$_r$NR$^a$(CR$^a$R$^{a1}$)$_s$-Q$^1$, —(CR$^a$R$^{a1}$)$_r$C(O)(CR$^a$R$^{a1}$)$_s$-Q$^1$, —(CR$^a$R$^{a1}$)$_r$C(O)O(CR$^a$R$^{a1}$)$_s$-Q$^1$, —(CR$^a$R$^{a1}$)$_r$OC(O)(CR$^a$R$^{a1}$)$_s$-Q$^1$, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q$^1$, —(CR$^a$R$^{a1}$)$_r$NR$^a$C(O)(CR$^a$R$^{a1}$)$_s$-Q$^1$, —(CR$^a$R$^{a1}_2$)$_r$S(O)$_p$(CR$^a$R$^{a1}$)$_s$-Q$^1$, —(CR$^a$R$^{a1}$)$_r$SO$_2$NR$^a$(CR$^a$R$^{a1}$)$_s$-Q$^1$, or —(CR$^a$R$^{a1}$)$_r$NR$^a$SO$_2$(CR$^a$R$^{a1}$)$_s$-Q$^1$;

W is a bond or (CR$^a$R$^{a1}$)$_m$;

ring Z$^0$ is a 5–6 membered heterocycle consisting of carbon atoms, 0–2 carbonyls, and 0–3 ring heteroatoms selected from O, N, NR$^7$, and S(O)$_p$;

X is absent or is C$_{1-3}$ alkylene;

U$^a$ is absent or is O, NR$^{a1}$, C(O), CR$^a$(OH), C(O)O, OC(O), C(O)NR$^{a1}$, NR$^{a1}$C(O), S(O)$_p$, S(O)$_p$NR$^{a1}$, or NR$^{a1}$S(O)$_p$;

X$^a$ is absent or is C$_{1-4}$ alkylene, C$_{2-4}$ alkenylene, or C$_{2-4}$ akynylene;

Y$^a$ is absent or is O or NR$^{a1}$;

R$^a$ is, independently at each occurrence, H, C$_{1-6}$ alkyl, phenyl, or benzyl;

R$^{a1}$ is, independently at each occurrence, H, C$_{1-6}$ alkyl, C$_{2-6}$ alkenyl, C$_{2-6}$ alkynyl, or —(CH$_2$)$_r$-3–8 membered carbocycle or heterocycle consisting of carbon atoms and 0–2 ring heteroatoms selected from N, NR$^{a2}$, O, and S(O)$_p$;

alternatively, R$^a$ and R$^{a1}$ when attached to a nitrogen, together with the nitrogen to which they are attached, combine to form a 5 or 6 membered heterocycle consisting of carbon atoms and 0–1 additional heteroatoms selected from N, NR$^{a2}$, O, and S(O)$_p$;

R$^c$ is, independently at each occurrence, H, Cl, F, Br, =O, —CN, NO$_2$, CF$_3$, —CF$_2$CF$_3$, CH$_2$F, CHF$_2$, —(CR$^a$R$^{a1}$)$_r$OR$^a$, —(CR$^a$R$^{a1}$)$_r$NR$^a$R$^{a1}$, —(CR$^a$R$^{a1}$)$_r$C (O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, —(CH$_2$)$_r$—C$_{3-6}$ carbocycle substituted with 0–2 R$^{c1}$, or —(CH$_2$)$_r$-5–6 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^d$ is, independently at each occurrence, C$_{1-6}$ alkyl, —OR$^a$, Cl, F, Br, I, =O, —CN, NO$_2$, —NR$^a$R$^{a1}$, —C(O)R$^a$, —C(O)OR$^a$, —C(O)NR$^a$R$^{a1}$, —S(O)$_2$NR$^a$R$^{a1}$, —NR$^a$S(O)$_2$R$^{a3}$, —S(O)$_p$R$^{a3}$, CF$_3$, C$_{3-6}$ carbocycle, or a 5–6 membered heterocycle consisting of carbon atoms and 1–4 heteroatoms selected from the group consisting of N, O, and S(O)$_p$;

R$^4$ is H, C$_{1-4}$ alkyl, C$_{2-4}$ alkenyl, or C$_{2-4}$ alkynyl;

R$^5$ is H, C$_{1-4}$ alkyl, C$_{2-4}$ alkenyl, or C$_{24}$ alkynyl;

R$^6$ is, independently at each occurrence, H, Cl, F, Br, I, =O, —CN, NO$_2$, CF$_3$, —CF$_2$CF$_3$, —(CR$^a$R$^{a1}$)$_r$OR$^a$, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)R$^a$, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$; and R$^7$ is, independently at each occurrence, H, —(CR$^a$R$^{a1}$)$_t$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_t$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$.

3. A compound according to claim 2, wherein:

R$^1$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_t$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_t$NR$^a$C(O)(CR$^a$R$^{a1}$)$_s$-Q, —(CR$^a$R$^{a1}$)$_r$S(CR$^a$R$^{a1}$)$_s$-Q, —(CR$^a$R$^{a1}$)$_r$S(O)(CR$^a$R$^{a1}$)$_s$-Q, —(CR$^a$R$^{a1}$)$_r$S(O)$_2$(CR$^a$R$^{a1}$)$_s$-Q, —(CR$^a$R$^{a1}$)$_r$SO$_2$NR$^a$(CR$^a$R$^{a1}$)$_s$-Q, or —(CR$^a$R$^{a1}$)$_t$NR$^a$SO$_2$(CR$^a$R$^{a1}$)$_s$-Q;

R$^2$ is Q$^1$, —C$_{1-6}$ alkylene-Q$^1$, —C$_{2-6}$ alkenylene-Q$^1$, —C$_{2-6}$ alkynylene-Q$^1$, —(CR$^a$R$^{a1}$)$_r$O(CR$^a$R$^{a1}$)$_s$-Q$^1$, —(CR$^a$R$^{a1}$)$_r$NR$^a$(CR$^a$R$^{a1}$)$_s$-Q$^1$, —(CR$^a$R$^{a1}$)$_r$C(O)(CR$^a$R$^{a1}$)$_s$-Q$^1$, —(CR$^a$R$^{a1}$)$_r$C(O)O(CR$^a$R$^{a1}$)$_s$-Q$^1$, —(CR$^a$R$^{a1}$)$_r$OC(O)(CR$^a$R$^{a1}$)$_s$-Q$^1$, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q$^1$, —(CR$^a$R$^{a1}$)$_r$NR$^a$C(O)(CR$^a$R$^{a1}$)$_s$-Q$^1$, —(CR$^a$R$^{a1}$_2$)$_r$S(O)$_p$(CR$^a$R$^{a1}$)$_s$-Q$^1$, —(CR$^a$R$^{a1}$)$_r$SO$_2$NR$^a$(CR$^a$R$^{a1}$)$_s$-Q$^1$, or —(CR$^a$R$^{a1}$)$_r$NR$^a$SO$_2$(CR$^a$R$^{a1}$)$_s$-Q$^1$;

R$^3$ is Q, —C$_{1-6}$ alkylene-Q, —C$_{2-6}$ alkenylene-Q, —C$_{2-6}$ alkynylene-Q, —(CH$_2$)$_r$O(CH$_2$)$_s$-Q, —(CH$_2$)$_r$NR$^a$(CH$_2$)$_s$-Q, —(CH$_2$)$_r$C(O)(CH$_2$)$_s$-Q, —(CH$_2$)$_r$C(O)O(CH$_2$)$_s$-Q, —(CH$_2$)$_r$C(O)NR$^a$R$^{a1}$, —(CH$_2$)$_r$C(O)NR$^a$(CH$_2$)$_s$-Q, —(CH$_2$)$_r$NR$^a$C(O)(CH$_2$)$_s$-Q, —(CH$_2$)$_r$S(O)$_p$(CH$_2$)$_s$-Q, —(CH$_2$)$_r$SO$_2$NR$^a$(CH$_2$)$_s$-Q, or —(CH$_2$)$_r$NR$^a$SO$_2$(CH$_2$)$_s$-Q;

Q is, independently at each occurrence, H, a C$_{3-10}$ carbocycle substituted with 0–3 R$^d$ or a 5–10 membered heterocycle consisting of carbon atoms and 1–4 heteroatoms selected from the group consisting of N, O, and S(O)$_p$, and substituted with 0–3 R$^d$;

Q$^1$ is, independently at each occurrence, H, a C3-10 carbocycle substituted with 0–3 R$^d$ or a 5–10 membered heterocycle consisting of carbon atoms and 1–4 heteroatoms selected from the group consisting of N, O, and S(O)$_p$, and substituted with 0–3 R$^d$;

ring Z$^0$ is a 5–6 membered heterocycle substituted with 0–2 R$^6$ and selected from: oxazolyl, isoxazolyl, dihydroisoxazolyl, thiazolyl, isothiazolyl, oxadiazolyl, thiadiazolyl, imidazolyl, imidazolinyl, imidazolidnyl, pyrrolyl, pyrrolinyl, furanyl, thienyl, pyridyl, pyrimidinyl, pyridazinyl, pyrazinyl, pyrazolyl, furyl, and triazoyl;

U$^a$ is absent or is O, NR$^{a1}$, C(O), C(O)NR$^{a1}$, NR$^{a1}$C(O), S(O)$_p$, S(O)$_p$NR$^{a1}$, or NR$^{a1}$S(O)$_p$;

X is absent or is methylene or ethylene;

Z is a C$_{3-8}$ cycloalkyl substituted with 0–5 R$^b$, a C$_{3-8}$ cycloalkenyl substituted with 0–5 R$^b$, phenyl substituted with 0–4 R$^b$, naphthyl substituted with 0–5 R$^b$, or a 5–14 membered heterocycle consisting of carbon atoms and 1–4 heteroatoms selected from the group consisting of N, O, and S(O)$_p$ and substituted with 0–5 R$^b$;

U$^a$ is absent or is O, NR$^{a1}$, C(O), C(O)NR$^{a1}$, NR$^{a1}$C(O), S(O)$_p$, S(O)$_p$NR$^{a1}$, or NR$^{a1}$S(O)$_p$;

R$^{a3}$, independently at each occurrence, H, C$_{1-6}$ alkyl, C$_{2-6}$ alkenyl, or —(CH$_2$)$_r$-3–8 membered carbocyclic or heterocyclic ring consisting of carbon atoms and 0–2 ring heteroatoms selected from N, NR$^{a2}$, O, and S(O)$_p$ and substituted with 0–3 R$^{c1}$;

R$^c$ is, independently at each occurrence, H, Cl, F, Br, =O, CF$_3$, —CF$_2$CF$_3$, CH$_2$F, CHF$_2$, —(CR$^a$R$^{a1}$)$_r$OR$^a$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl, C$_{2-6}$ alkenyl, C$_{2-6}$ alkynyl, —(CH$_2$)$_r$—C$_{3-6}$ cycloalkyl substituted with 0–1 R$^{c1}$, phenyl substituted with 0–2 R$^{c1}$, or —(CH$_2$)$_r$-5–6 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^d$ is, independently at each occurrence, $C_{1-6}$ alkyl, —$OR^a$, Cl, F, Br, I, =O, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, $CF_3$, or phenyl;

$R^4$ is H;

$R^5$ is H;

$R^6$ is, independently at each occurrence, H, Cl, F, Br, I, =O, —CN, $NO_2$, $CF_3$, —$CF_2CF_3$, —$(CR^aR^{a1})_rOR^a$, —$(CR^aR^{a1})_rNR^aR^{a1}$, —$(CR^aR^{a1})_rC(O)R^a$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_sS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

r, at each occurrence, is selected from 0, 1, 2, and 3;

s, at each occurrence, is selected from 0, 1, 2, and 3; and t, at each occurrence, is selected from 1, 2, and 3.

4. A compound according to claim 3, wherein:

$R^1$ is Q, —$C_{1-6}$ alkylene-Q, —$C_{2-6}$ alkenylene-Q, —$C_{2-6}$ alkynylene-Q, —$(CH_2)_tO(CH_2)_s$-Q, —$(CH_2)_tNR^a$ $(CH_2)_s$-Q, —$(CH_2)_rC(O)(CH_2)_s$-Q, —$(CH_2)_rC(O)O$ $(CH_2)_s$-Q, —$(CH_2)_rC(O)NR^aR^{a1}$, —$(CH_2)_rC(O)NR^a$ $(CH_2)_s$-Q, —$(CH_2)_rS(CH_2)_s$-Q, —$(CH_2)_rS(O)(CH_2)_s$-Q, —$(CH_2)_rS(O)_2(CH_2)_s$-Q, —$(CH_2)_rSO_2NR^a(CH_2)_s$-Q, or —$(CH_2)_tNR^aSO_2(CH_2)_s$-Q;

$R^2$ is Q, —$C_{1-6}$ alkylene-$Q^1$, —$C_{2-6}$ alkenylene-$Q^1$, —$C_{2-6}$ alkynylene-$Q^1$, —$(CH_2)_tO(CH_2)_s$-$Q^1$, —$(CH_2)_tNR^a$ $(CH_2)_s$-$Q^1$, —$(CH_2)_rC(O)(CH_2)_s$-$Q^1$, —$(CH_2)_rC(O)O$ $(CH_2)_s$-$Q^1$, —$(CH_2)_rC(O)NR^aR^{a1}$, —$(CH_2)_rC(O)NR^a$ $(CH_2)_s$-$Q^1$, —$(CH_2)_rS(CH_2)_s$-$Q^1$, —$(CH_2)_rS(O)$ $(CH_2)_s$-$Q^1$, —$(CH_2)_rS(O)_2(CH_2)_s$-$Q^1$, —$(CH_2)_t$ $SO_2NR^a(CH_2)_s$-$Q^1$, or —$(CH_2)_tNR^aSO_2(CH_2)_s$-$Q^1$;

$R^3$ is H, $C_{1-4}$ alkyl, $C_{2-4}$ alkenyl, $C_{2-4}$ alkynyl, phenyl, or benzyl;

Q is, independently at each occurrence, H, a $C_{3-6}$ cycloalkyl substituted with 0–2 $R^d$, phenyl substituted with 0–3 $R^d$ or a 5–6 membered heterocycle consisting of carbon atoms and 1–4 heteroatoms selected from the group consisting of N, O, and $S(O)_p$, and substituted with 0–3 $R^d$;

$Q^1$ is, independently at each occurrence, H, a $C_{3-6}$ cycloalkyl substituted with 0–2 $R^d$, phenyl substituted with 0–3 $R^d$ or a 5–6 membered heterocycle consisting of carbon atoms and 1–4 heteroatoms selected from the group consisting of N, O, and $S(O)_p$, and substituted with 0–3 $R^d$;

Z is a $C_{4-8}$ cycloalkyl substituted with 0–3 $R^b$, a $C_{4-8}$ cycloalkenyl substituted with 0–3 $R^b$, phenyl substituted with 0–4 $R^b$, naphthyl substituted with 0–5 $R^b$, or a heterocycle substituted with 0–3 $R^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl;

$Z^a$ is phenyl substituted with 0–3 $R^c$, naphthyl substituted with 0–3 $R^c$, or a heterocycle substituted with 0–3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

$R^a$ is, independently at each occurrence, H, $C_{1-6}$ alkyl, phenyl, or benzyl;

$R^{a1}$ is, independently at each occurrence, H, $C_{1-6}$ alkyl, phenyl, or benzyl;

$R^{a3}$ is, independently at each occurrence, H, $C_{1-6}$ alkyl, phenyl, or benzyl;

$R^c$ is, independently at each occurrence, H, Cl, F, Br, =O, $CF_3$, —$CF_2CF_3$, $CH_2F$, $CHF_2$, —$(CR^aR^{a1})_rOR^a$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_sS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or a 5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds; and $R^6$ is, independently at each occurrence, H, Cl, F, Br I, =O, —CN, $NO_2$, $CF_3$, —$CF_2CF_3$, —$(CR^aR^{a1})_rOR^a$, —$(CR^aR^{a1})_rNR^aR^{a1}$, —$(CR^aR^{a1})_rC(O)(CR^aR^{a1})_sR^e$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_sS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, —$(CR^aR^{a1})_rC_{3-7}$ carbocycle substituted with 0–2 $R^{c1}$, or —$(CR^aR^{a1})_r$-5–6 membered heterocycle consisting of carbon atoms and 1–4 heteroatoms selected from the group consisting of N, O, and $S(O)_p$, and substituted with 0–2 $R^{c1}$.

5. A compound according to claim 4, wherein:

$R^1$ is Q, —$C_{1-6}$ alkylene-Q, —$C_{2-6}$ alkenylene-Q, or —$C_{2-6}$ alkynylene-Q;

Q is, independently at each occurrence, H, phenyl substituted with 0–2 $R^d$, or a 5–6 membered heterocycle consisting of carbon atoms and 1–4 heteroatoms selected from the group consisting of N, O, and $S(O)_p$, and substituted with 0–2 $R^d$;

L is a bond, CO or $CH_2$;

X is absent or is methylene;

Y is absent or is O;

Z is phenyl substituted with 0–3 $R^b$ or a heterocycle substituted with 0–2 $R^b$ and selected from the group: thienyl, Furanyl, pyridyl, pyrazinyl, pyrimidinyl, thiazolyl, oxazolyl, isoxazolyl, and imidazolyl;

$U^a$ is absent or is O;

$X^a$ is absent or is $C_{1-4}$ alkylene, $C_{2-4}$ alkenylene, or $C_{2-4}$ alkynylene;

$Y^a$ is absent or is O;

$R^a$ is, independently at each occurrence, H or $C_{1-4}$ alkyl;

$R^{a1}$ is, independently at each occurrence, H or $C_{1-4}$ alkyl;

$R^{a3}$, independently at each occurrence, H, $C_{1-4}$ alkyl, phenyl, or benzyl;

$R^c$ is, independently at each occurrence, H, $C_{1-6}$ alkyl, $C_{2-6}$ alkenyl, $C_{2-6}$ alkynyl, Cl, F, Br, =O, $CF_3$, $CH_2F$, $CHF_2$, $-(CR^aR^{a1})_rOR^a$, $-(CR^aR^{a1})_rNR^aR^{a1}$, $-(CR^aR^{a1})_rC(O)R^{a1}$, $-(CR^aR^{a1})_rC(O)OR^{a1}$, $-(CR^aR^{a1})_rC(O)NR^aR^{a1}$, $-(CR^aR^{a1})_rNR^aC(O)R^{a1}$, $-(CR^aR^{a1})_rS(O)_pR^{a3}$, $-(CR^aR^{a1})_rSO_2NR^aR^{a1}$, $-(CR^aR^{a1})_rNR^aSO_2R^{a3}$, or phenyl;

alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^e$ is, independently at each occurrence, H, $C_{1-6}$ alkyl, $C_{1-6}$ alkoxy, phenoxy, benzoxy, $C_{3-6}$ carbocycle substituted with 0–2 $R^{c1}$, and a 5–6 membered heterocycle consisting of carbon atoms and 1–4 heteroatoms selected from the group consisting of N, O, and $S(O)_p$, and substituted with 0–2 $R^{c1}$; and $R^6$ is, independently at each occurrence, H, Cl, F, Br, I, =O, —CN, $NO_2$, $CF_3$, $-CF_2CF_3$, $-(CH_2)_rOR^a$, $-(CH_2)_rNR^aR^{a1}$, $-(CH_2)_rC(O)R^a$, $-(CH_2)_rC(O)(CH_2)_sR^e$, $-(CH_2)_rC(O)OR^{a1}$, $-(CH_2)_rC(O)NR^aR^{a1}$, $-(CH_2)_rS(O)_pR^{a3}$, $-(CH_2)_rSO_2NR^aR^{a1}$, $C_{1-4}$ alkyl substituted with 0–1 $R^{c1}$, $C_{2-4}$ alkenyl substituted with 0–1 $R^{c1}$, $C_{2-4}$ alkynyl substituted with 0–1 $R^{c1}$, $-(CH_2)_r-C_{3-6}$ carbocycle substituted with 0–2 $R^{c1}$, or $-(CH_2)_r$-5–6 membered heterocycle consisting of carbon atoms and 1–4 heteroatoms selected from the group consisting of N, O, and $S(O)_p$, and substituted with 0–2 $R^{c1}$.

6. A compound according to claim 5, wherein:

Z is phenyl substituted with 0–1 $R^b$;

$Z^a$ is phenyl substituted with 0–3 $R^c$, naphthyl substituted with 0–3 $R^c$, or a heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

$R^b$ is, independently at each occurrence, $C_{1-6}$ alkyl, $-OR^a$, Cl, F, Br, $-NR^aR^{a1}$, $-C(O)R^a$, $-C(O)OR^a$, $-C(O)NR^aR^{a1}$, $-S(O)_2NR^aR^{a1}$, $-NR^aS(O)_2R^{a3}$, $-S(O)_pR^{a3}$, or $CF_3$;

$R^c$ is, independently at each occurrence, H, $C_{1-6}$ alkyl, $C_{2-6}$ alkenyl, $C_{2-6}$ alkynyl, Cl, F, Br, =O, $CF_3$, $-(CH_2)_rOR^a$, $-(CH_2)_rNR^aR^{a1}$, $-(CH_2)_rC(O)R^{a1}$, $-(CH_2)_rC(O)OR^{a1}$, $-(CH_2)_rC(O)NR^aR^{a1}$, $-(CH_2)_rNR^aC(O)R^{a1}$, $-(CH_2)_rS(O)_pR^{a3}$, $-(CH_2)_rSO_2NR^aR^{a1}$, or $-(CH_2)_rNR^aSO_2R^{a3}$;

alternatively, when two $R^c$ groups are attached to adjacent carbon atoms, together with the carbon atoms to which they are attached they form a 5–6 membered carbocyclic or heterocyclic ring consisting of: carbon atoms and 0–1 heteroatoms selected from the group consisting of N, O, and $S(O)_p$; and $R^e$ is, independently at each occurrence, H, $C_{1-6}$ alkyl, $C_{1-6}$ alkoxy, phenoxy, benzoxy, phenyl substituted with 0–1 $R^{c1}$, or a 5–6 membered heterocycle consisting of carbon atoms and 1–4 heteroatoms selected from the group consisting of N, O, and $S(O)_p$, and substituted with 0–1 $R^{c1}$.

7. A compound according to claim 6, wherein the compound is of Formula (Ia):

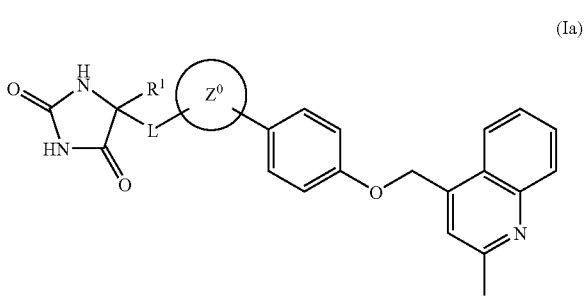

(Ia)

or a stereoisomer or pharmaceutically acceptable salt or solvate form thereof, wherein:

$R^1$ is H or $C_{1-4}$ alkyl;

L is a bond or $-CH_2-$;

ring $Z^0$ is 4,5-dihydroisoxazol-3-yl substituted with 0–1 $R^6$, 4,5-dihydroisoxazol-5-yl substituted with 0–1 $R^6$, isoxazol-3-yl substituted with 0–1 $R^6$, or isoxazol-5-yl substituted with 0–1 $R^6$;

$R^6$ is H, $C_{1-4}$ alkyl, $-(CH_2)_rOH$, $-(CH_2)_rNH_2$, $-(CH_2)_rNHCO(C_{1-4}$ alkyl), $-(CH_2)_rNHCOO(C_{1-4}$ alkyl), $-(CH_2)_rNHSO_2(C_{1-4}$ alkyl), $-(CH_2)_r$-phenyl substituted with 0–1 $R^{c1}$, $-(CH_2)_r$-5–6 membered heterocycle consisting of carbon atoms and 1–4 heteroatoms selected from the group consisting of N, O, and $S(O)_p$, and substituted with 0–1 $R^{c1}$, $-(CH_2)_r-NHCO$-phenyl substituted with 0–1 $R^{c1}$, or $-(CH_2)_r-NHCO$-5–6 membered heterocycle consisting of carbon atoms and 1–4 heteroatoms selected from the group consisting of N, O, and $S(O)_p$, and substituted with 0–1 $R^{c1}$; and r, at each occurrence, is 0 or 1.

8. A compound according to claim 7, wherein:

$R^1$ is H or Me;

L is a bond or $-CH_2-$; and $R^6$ is H, Me, i-Pr, $-CH_2OH$, $-CH_2NH_2$, $-CH_2NHCOMe$, $-CH_2NHBoc$, $-CH_2NHSO_2Me$, 5-thiophen-2-yl, 5-morpholin-4-ylmethyl, $-CH_2NHCO$-phenyl, or $-CH_2NHCO$-4-pyridyl.

9. A compound of claim 1 selected from:

5-{3-[4-(2-methylquinolin-4-yl-methoxy)phenyl]-4,5-dihydroisoxazol-5-yl}imidazolidine-2,4-dione trifluoroacetate;

5-{5-methyl-3-[4-(2-methylquinolin-4-yl-methoxy)phenyl]4,5-dihydroisoxazol-5-yl}imidazolidine-2,4-dione trifluoroacetate;

5-methyl-5-{5-[4-(2-methyl-quinolin-4-ylmethoxy)-phenyl]-4,5-dihydro-isoxazol-3-yl}-imidazolidine-2,4-dione trifluoroacetate;

5-methyl-5-{5-methyl-5-[4-(2-methyl-quinolin-4-yl-methoxy)-phenyl]-4,5-dihydro-isoxazol-3-yl}-imidazolidine-2,4-dione trifluoroacetate;

5-methyl-5-{5-[4-(2-methyl-quinolin-4-ylmethoxy)-phenyl]-5-thiophen-2-yl-4,5-dihydro-isoxazol-3-yl}-imidazolidine-2,4-dione;

5-{5-isopropyl-5-[4-(2-methylquinolin-4-yl-methoxy)phenyl]-4,5-dihydroisoxazol-3-yl}-5-methylimidazolidine-2,4-dione trifluoroacetate;

{3-(4-methyl-2,5-dioxo-imidazolidin-4-yl)-5-[4-(2-methyl-quinolin-4-ylmethoxy)-phenyl]-4,5-dihydro-isoxazol-5-ylmethyl}-carbamic acid tert-butyl ester trifluoroacetate;

5-{5-aminomethyl-5-[4-(2-methyl-quinolin-4-yl-methoxy)-phenyl]-4,5-dihydro-isoxazol-3-yl}-5-methyl-imidazolidine-2,4-dione di-trifluoroacetate;

N-{3-(4-methyl-2,5-dioxo-imidazolidin-4-yl)-5-[4-(2-methyl-quinolin-4-ylmethoxy)-phenyl]-4,5-dihydro-isoxazol-5-ylmethyl}-acetamide trifluoroacetate;

N-{3-(4-methyl-2,5-dioxo-imidazolidin-4-yl)-5-[4-(2-methyl-quinolin-4-ylmethoxy)-phenyl]-4,5-dihydro-isoxazol-5-ylmethyl}-methanesulfonamide trifluoroacetate;

N-{3-(4-methyl-2,5-dioxo-imidazolidin-4-yl)-5-[4-(2-methyl-quinolin-4-ylmethoxy)-phenyl]-4,5-dihydro-isoxazol-5-ylmethyl}-isonicotinamide di-(trifluoroacetate);

N-{3-(4-methyl-2,5-dioxo-imidazolidin-4-yl)-5-[4-(2-methyl-quinolin-4-ylmethoxy)-phenyl]-4,5-dihydro-isoxazol-5-ylmethyl}-benzamide trifluoroacetate;

5-methyl-5-{5-[4-(2-methyl-quinolin-4-ylmethoxy)-phenyl]-5-morpholin-4-ylmethyl-4,5-dihydro-isoxazol-3-yl}-imidazolidine-2,4-dione di-trifluoroacetate;

5-{5-hydroxymethyl-5-[4-(2-methyl-quinolin-4-yl-methoxy)-phenyl]-4,5-dihydro-isoxazol-3-yl}-5-methyl-imidazolidine-2,4-dione trifluoroacetate; and 5-methyl-5-{5-[4-(2-methylquinolin-4-yl-methoxy)phenyl]-isoxazol-3-yl-methyl}imidazolidine-2,4-dione trifluoroacetate;

or a stereoisomer or a pharmaceutically acceptable salt or solvate form thereof.

10. A pharmaceutical composition, comprising: a pharmaceutically acceptable carrier and a therapeutically effective amount of a compound of claim 1, or a stereoisomer or a pharmaceutically acceptable salt or solvate form thereof.

11. A method for treating an inflammatory disorder, comprising: administering to a patient in need thereof a therapeutically effective amount of a compound of claim 1, or a stereoisomer or a pharmaceutically acceptable salt or solvate form thereof.

12. A method of treating a condition or disease mediated by MMPs, TACE, aggrecanase, or a combination thereof in a mammal, comprising: administering to the mammal in need of such treatment a therapeutically effective amount of a compound of claim 1, or a stereoisomer or a pharmaceutically acceptable salt or solvate form thereof.

13. A method comprising: administering a compound of claim 1, or a stereoisomer or a pharmaceutically acceptable salt or solvate form thereof, in an amount effective to treat a condition or disease mediated by MMPs, TACE, aggrecanase, or a combination thereof.

14. A method of treating according to claim 13, wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

15. A method for treating inflammatory disorders, comprising: administering, to a host in need of such treatment, a therapeutically effective amount of a compound of claim 1, or a pharmaceutically acceptable salt form thereof, in combination with one or more additional anti-inflammatory agents selected from selective COX-2 inhibitors, TNF-α inhibitors and TNF-α antibody or protein sequestration agents.

\* \* \* \* \*